(12) United States Patent
Ranish et al.

(10) Patent No.: US 8,227,251 B2
(45) Date of Patent: Jul. 24, 2012

(54) MASS SPECTRUM-BASED IDENTIFICATION AND QUANTITATION OF PROTEINS AND PEPTIDES

(75) Inventors: Jeff Ranish, Seattle, WA (US); Jie Luo, Seattle, WA (US); Wei Yan, Edmonds, WA (US)

(73) Assignee: Institute for Systems Biology, Seattle, WA (US)

( * ) Notice: Subject to any disclaimer, the term of this patent is extended or adjusted under 35 U.S.C. 154(b) by 171 days.

(21) Appl. No.: 12/760,500

(22) Filed: Apr. 14, 2010

(65) Prior Publication Data

US 2010/0261279 A1   Oct. 14, 2010

Related U.S. Application Data

(60) Provisional application No. 61/169,255, filed on Apr. 14, 2009.

(51) Int. Cl.
*G01N 33/68*   (2006.01)
(52) U.S. Cl. .............. 436/86; 436/56; 436/89; 436/173; 250/281; 250/282
(58) Field of Classification Search ............... 436/56, 436/86, 89, 173; 530/409; 250/281, 282
See application file for complete search history.

(56) References Cited

U.S. PATENT DOCUMENTS

| | | | |
|---|---|---|---|
| 6,670,194 B1 * | 12/2003 | Aebersold et al. | 436/173 |
| 7,045,296 B2 * | 5/2006 | Parker et al. | 435/7.1 |
| 2004/0106150 A1 * | 6/2004 | Wang | 435/7.1 |
| 2008/0050833 A1 | 2/2008 | Smith et al. | |
| 2009/0053742 A1 * | 2/2009 | Gygi et al. | 435/7.92 |

OTHER PUBLICATIONS

Yan et al. Molecular & Cellular Proteomics, vol. 10, No. 3, 2011, pp. 1-15.*
Colzani et al., Mol. Cell. Proteomics (2008) 7:927-937.
Desouza et al., J. Proteome Res. (2008) 7:3525-3534.
Domon et al., Science (2006) 312:212-217.
Hanke et al., J. Proteome Res. (2008) 7:1118-1130.
International Search Report for PCT/US10/31116, mailed on Jun. 28, 2010, 1 page.
Koehler et al., J. Proteome Res. (2009) 8(9):4333-41.
Ross et al., Mol. Cell. Proteomics (2004) 3:1154-1169.
Thompson et al., Anal. Chem. (2003) 75:1895-1904.
Written Opinion of the International Searching Authority for PCT/US10/31116, mailed on Jun. 28, 2010, 10 pages.
Yan et al., Briefings in Functional Genomics and Proteomics (2005) 4:27-38.

* cited by examiner

*Primary Examiner* — Maureen Wallenhorst
(74) *Attorney, Agent, or Firm* — Morrison & Foerster LLP

(57) ABSTRACT

The present invention relates to methods for analyzing complex mixtures of proteins, both for identification and quantitation of proteins of interest, and in particular, methods of identification and quantitation of proteins present at low levels, using internal standard peptides isobarically tagged at the N and C termini.

35 Claims, 21 Drawing Sheets

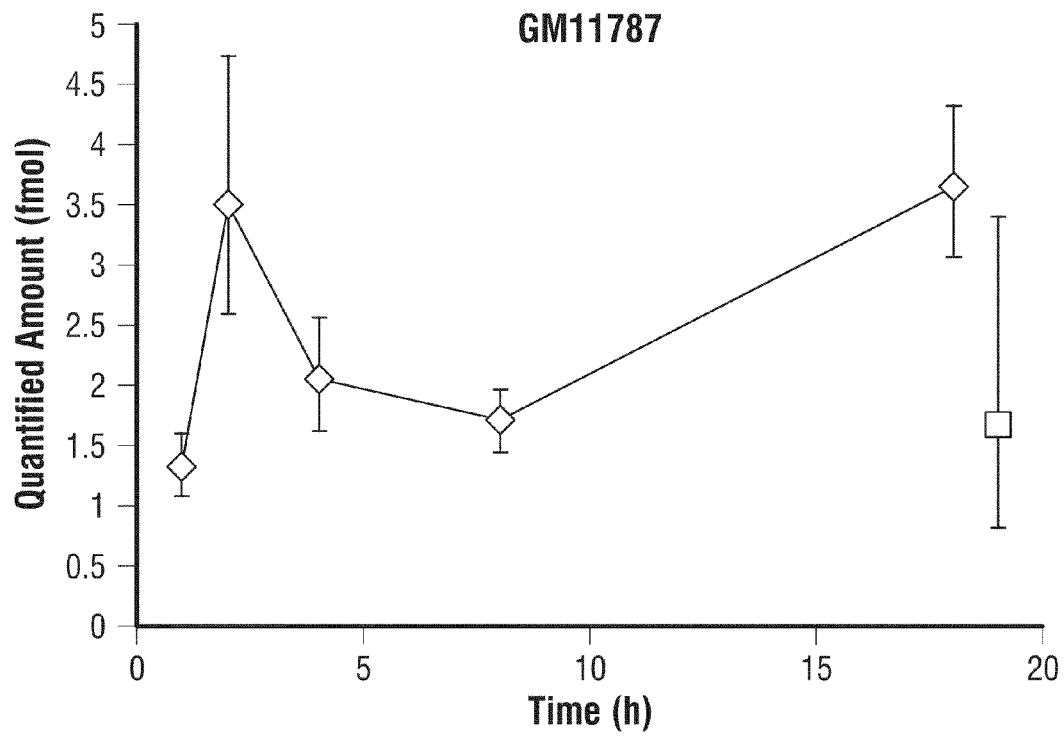
FIG. 8A (1)
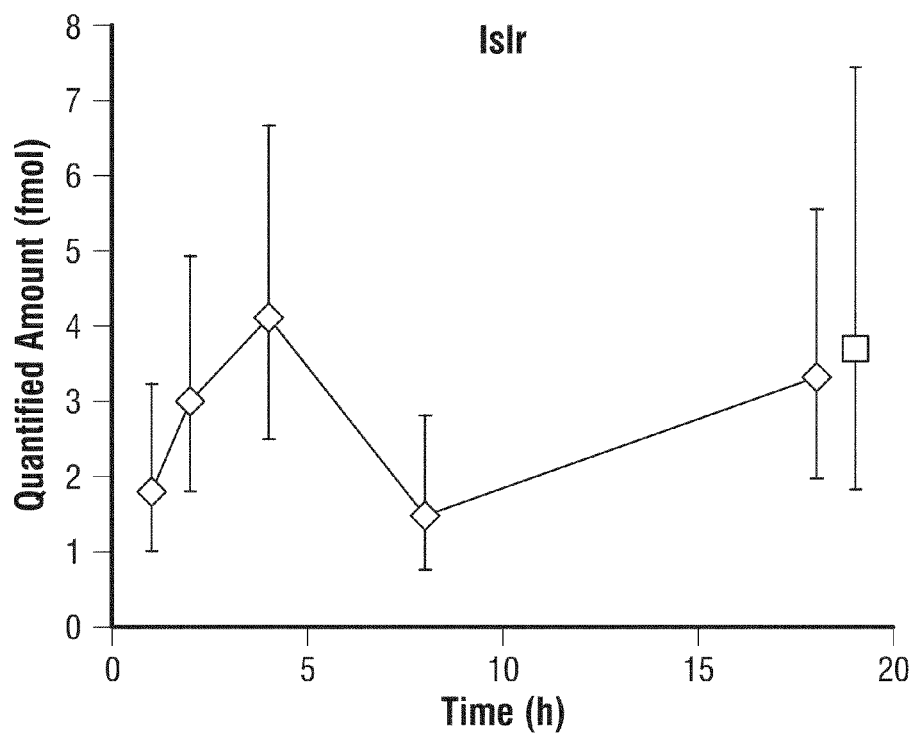
FIG. 8A (2)

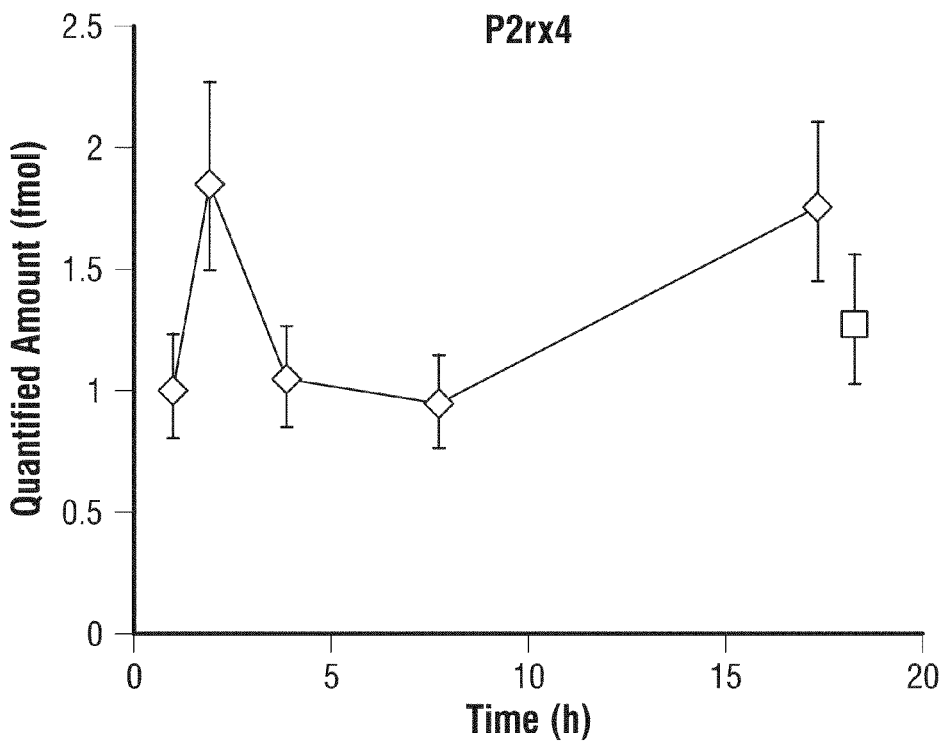
FIG. 8A (3)
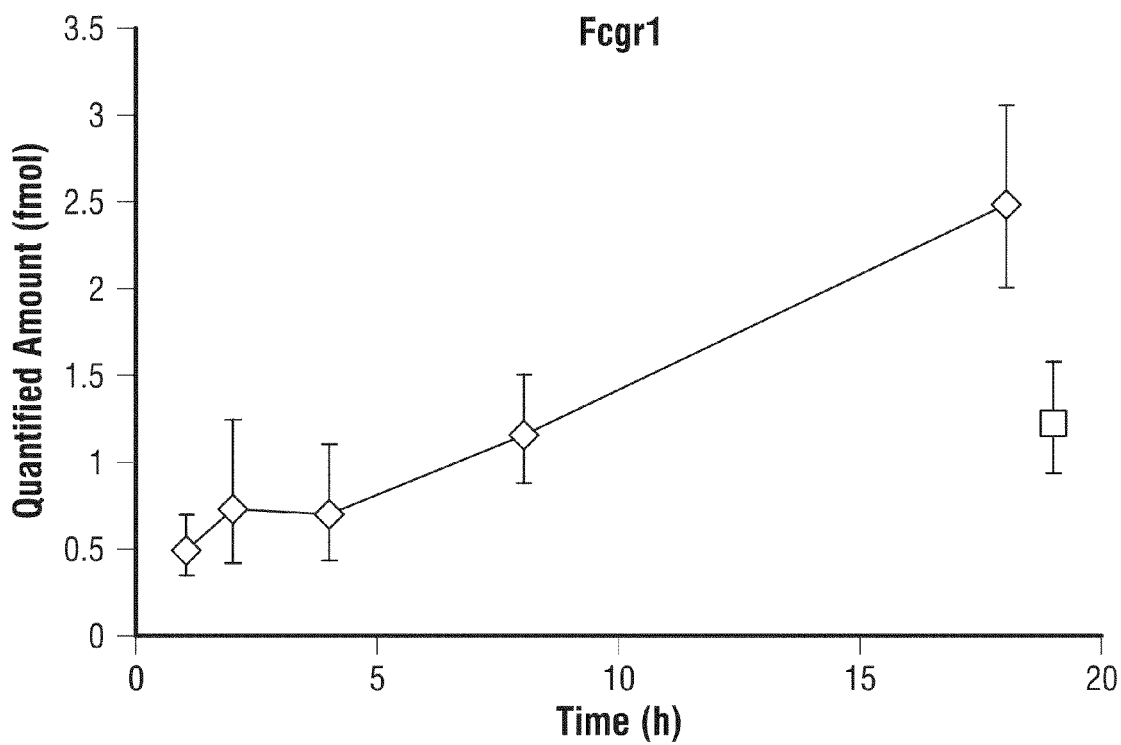
FIG. 8B (1)

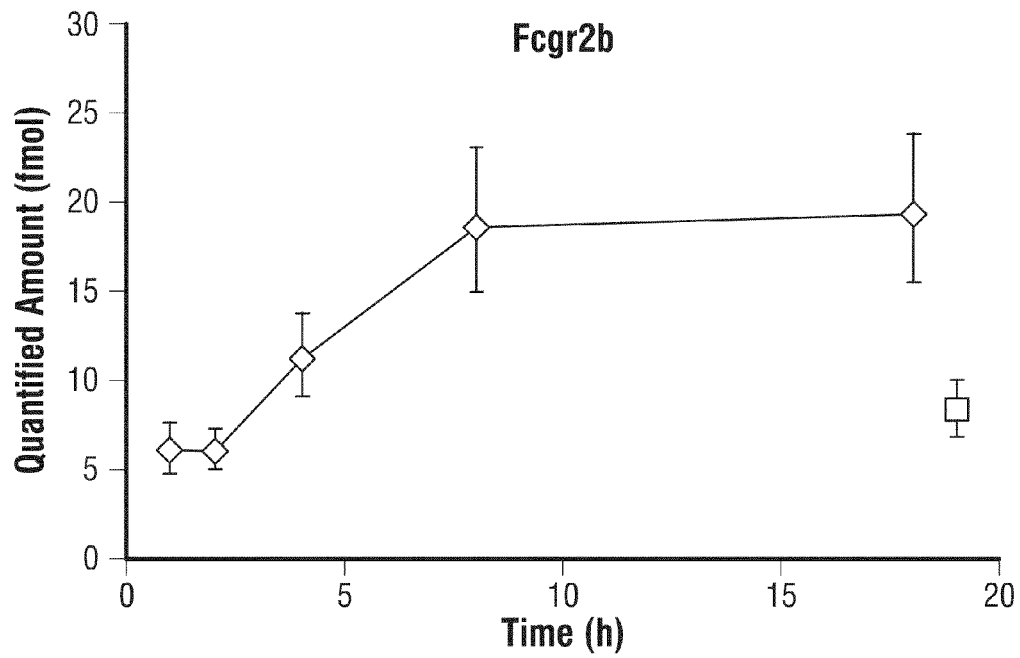
FIG. 8B (2)
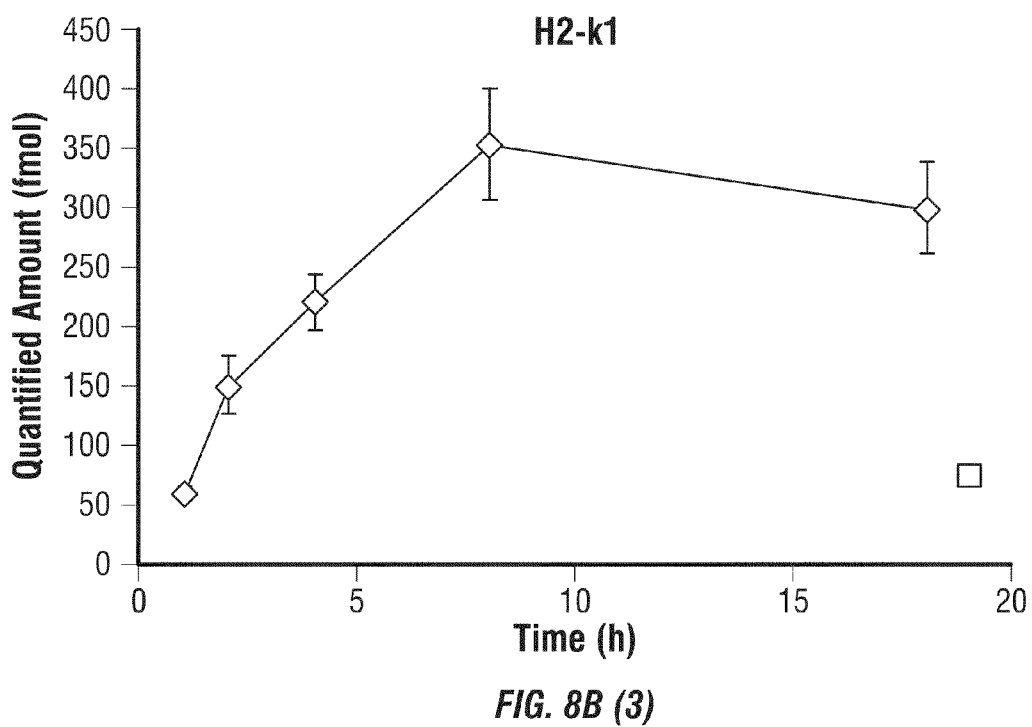
FIG. 8B (3)

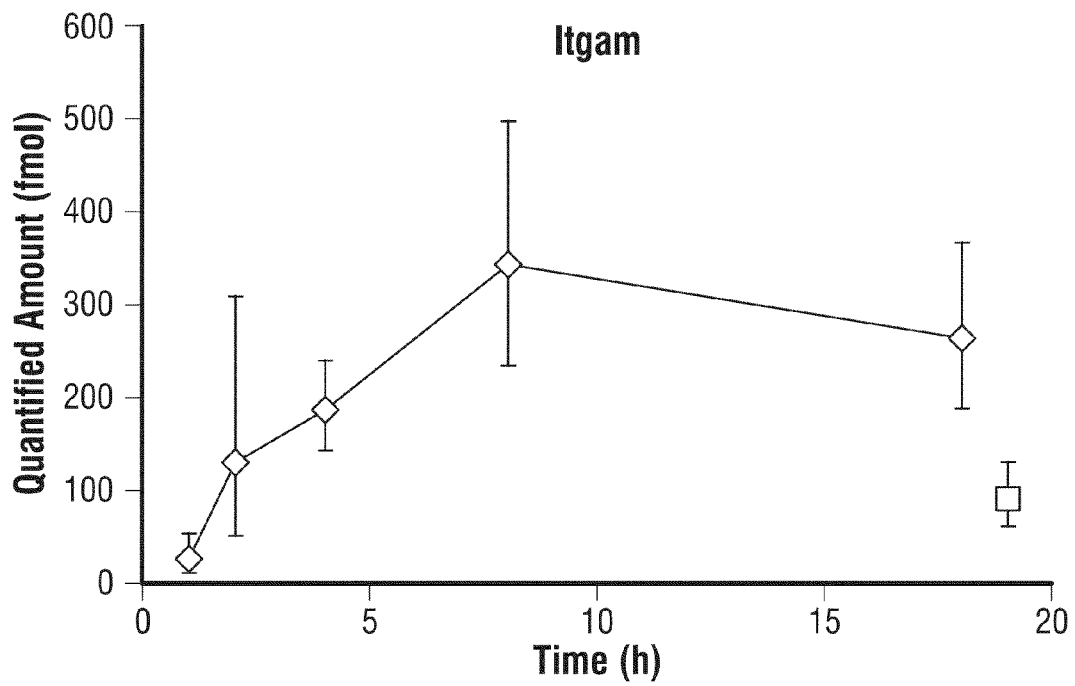
FIG. 8B (4)
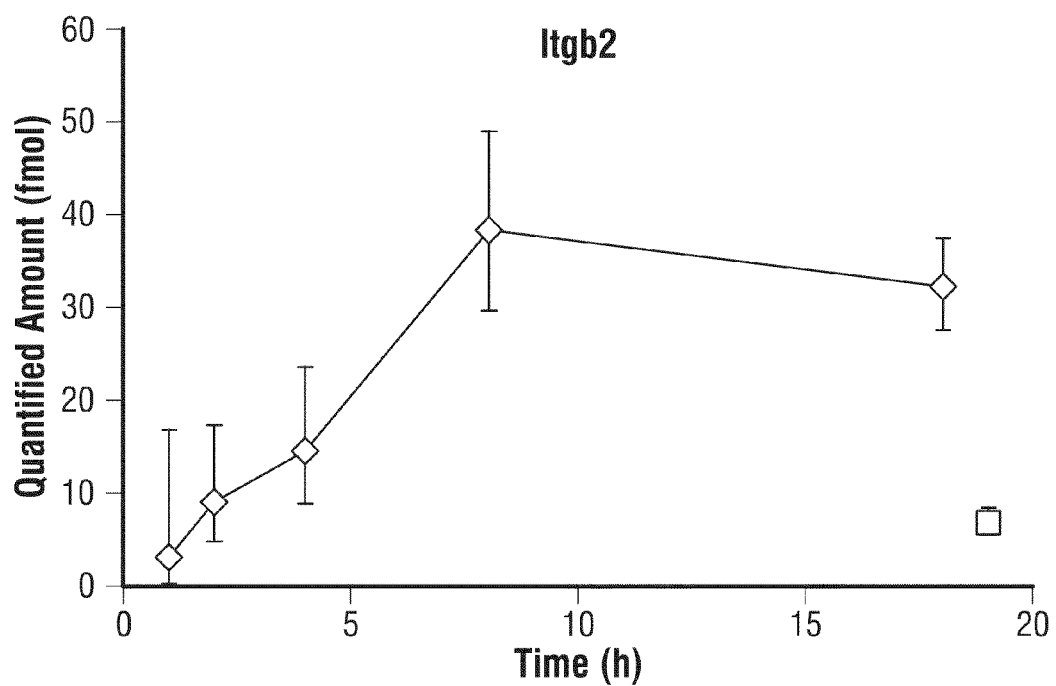
FIG. 8B (5)

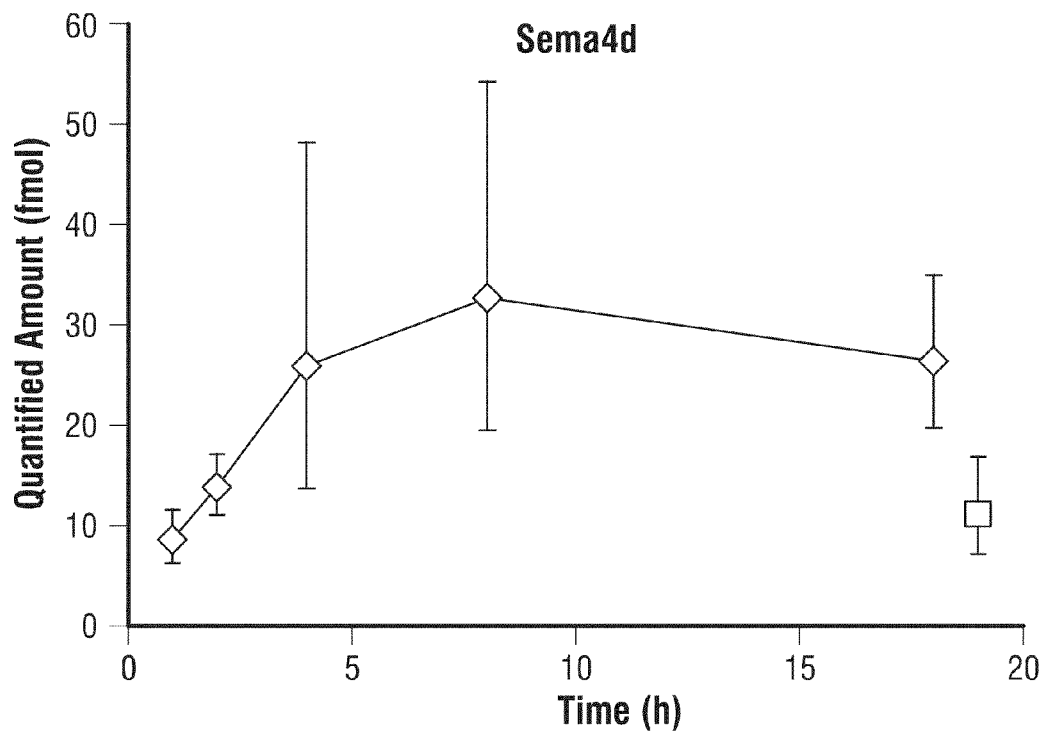
FIG. 8B (6)
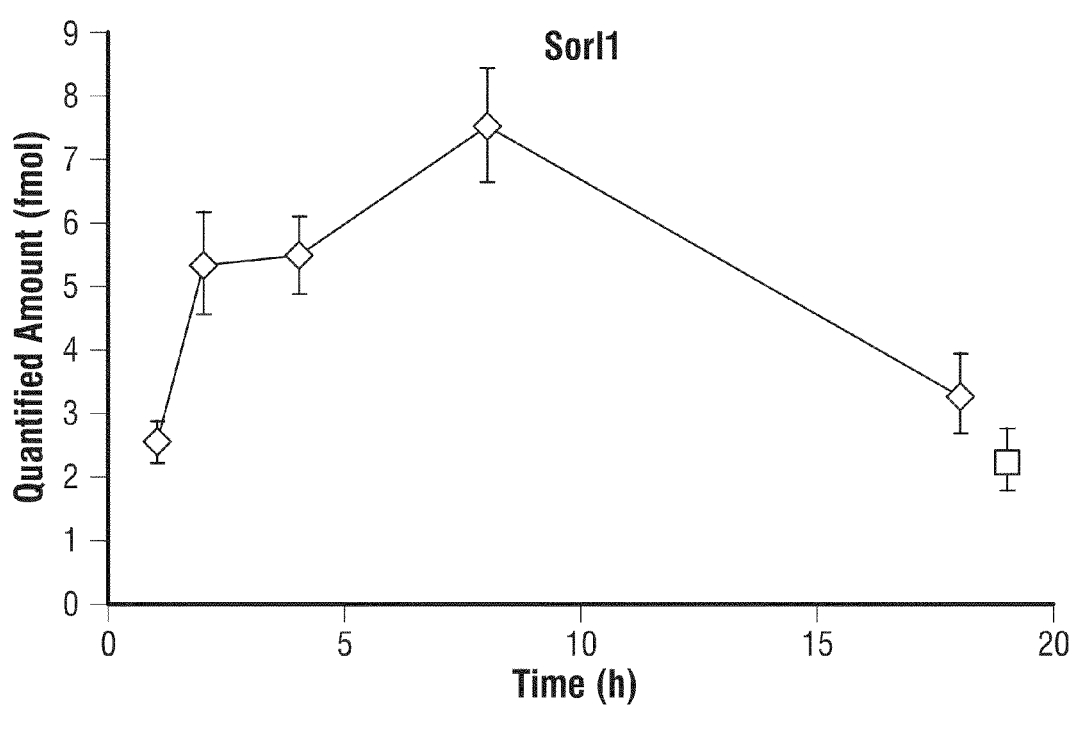
FIG. 8B (7)

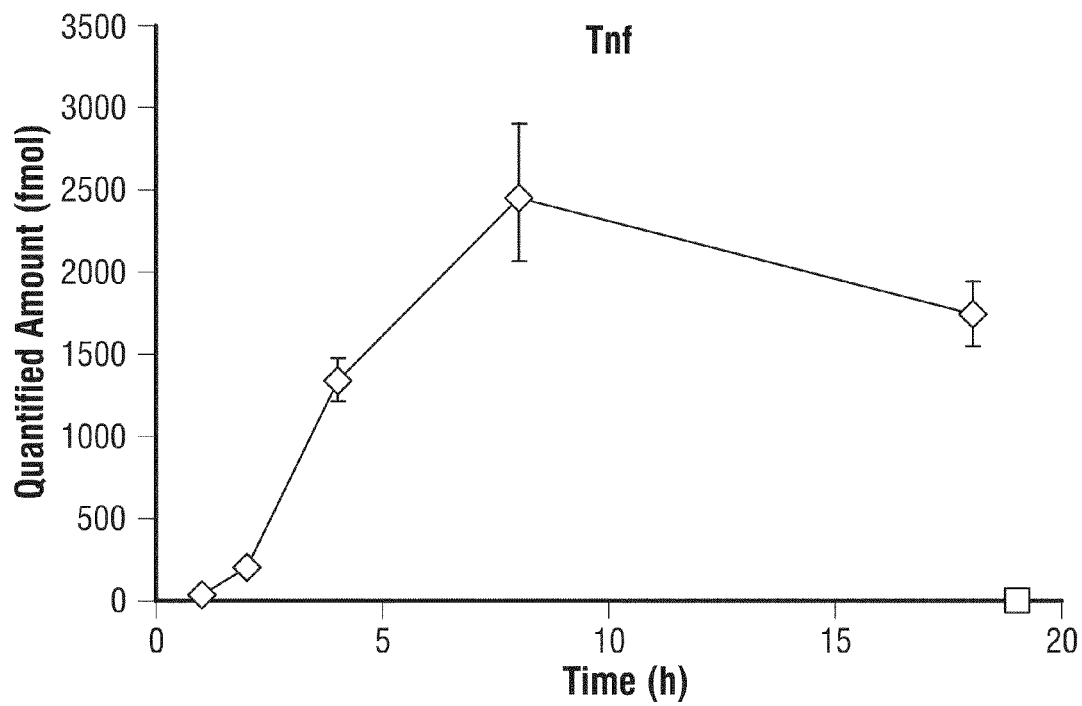
FIG. 8B (8)
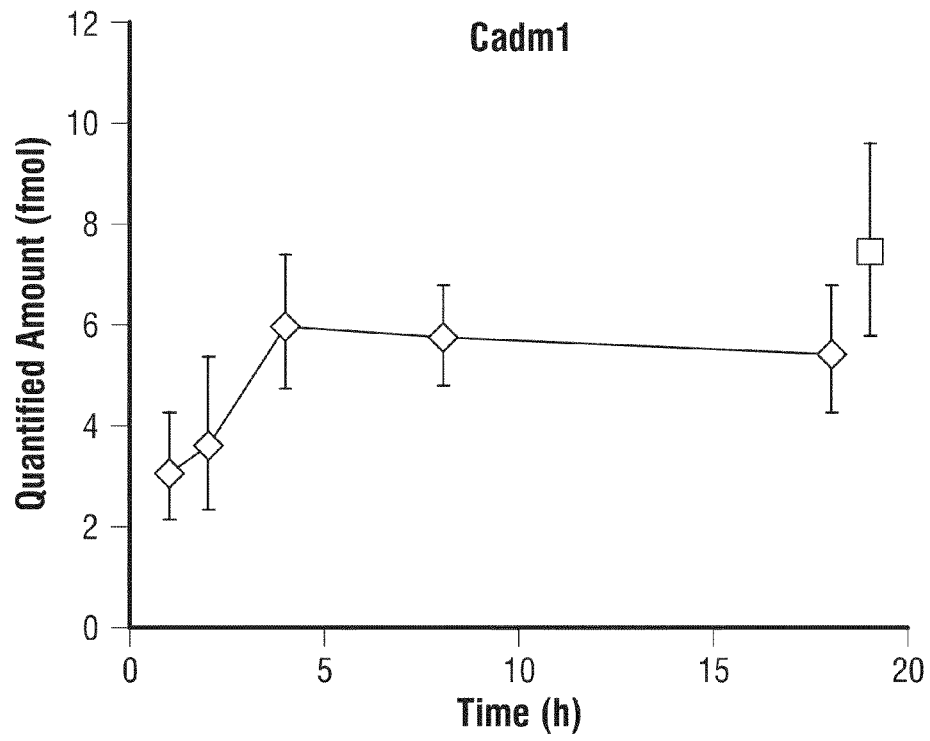
FIG. 8C (1)

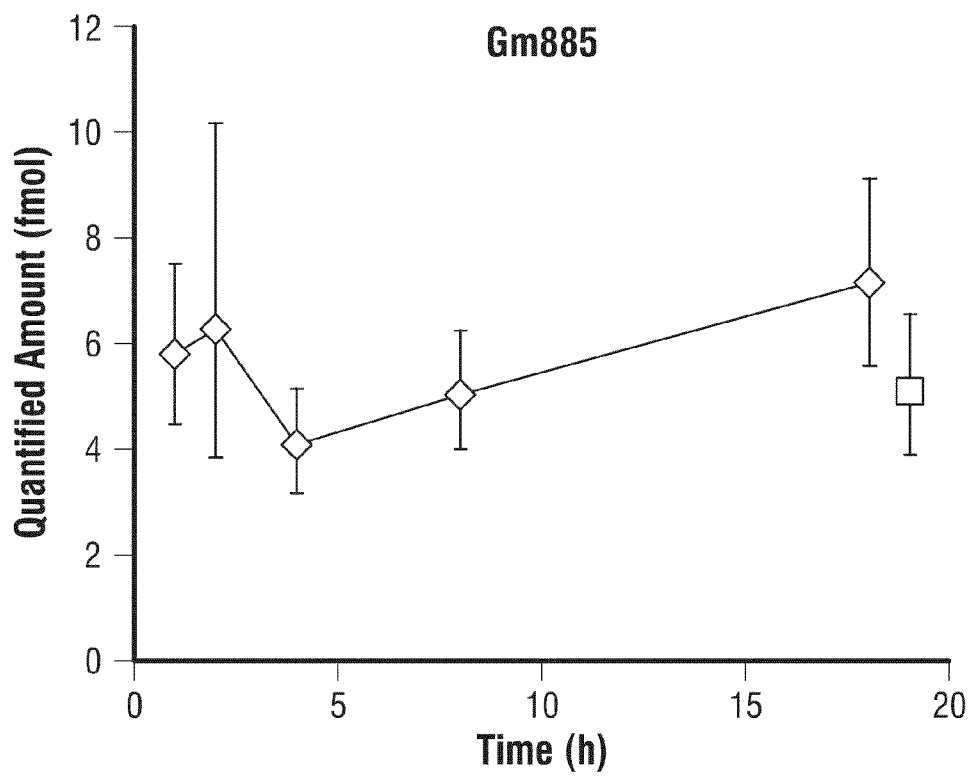
FIG. 8C (2)
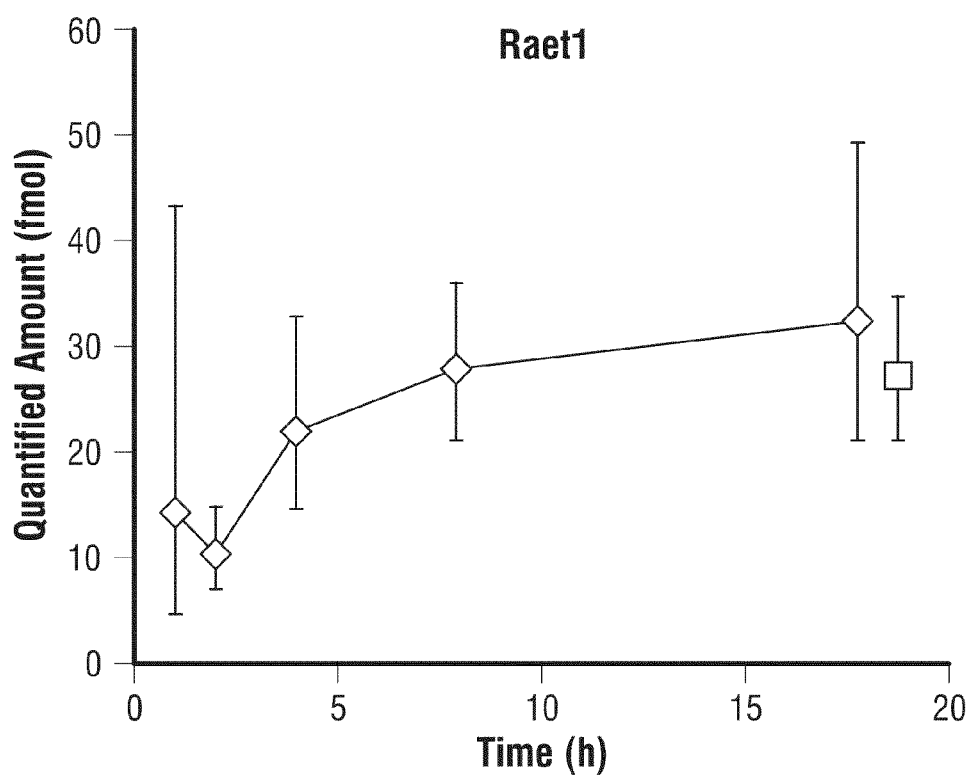
FIG. 8C (3)

MASS SPECTRUM-BASED IDENTIFICATION AND QUANTITATION OF PROTEINS AND PEPTIDES

CROSS-REFERENCE TO RELATED APPLICATIONS

This application claims priority from U.S. provisional application 61/169,255 filed Apr. 14, 2009. The contents of this document are incorporated herein by reference.

STATEMENT OF RIGHTS TO INVENTIONS MADE UNDER FEDERALLY SPONSORED RESEARCH

This work was supported in part by grants numbered P50 GM076547 and N01-HV-28179 from the National Institutes of Health. The U.S. government has certain rights in this invention.

TECHNICAL FIELD

The invention concerns methods for analyzing complex mixtures of proteins, both for identification and quantitation of proteins of interest. More particularly, it concerns improvements that permit identification and quantitation of species present at very low levels.

BACKGROUND ART

The success of proteomics research depends on the ability to reliably identify and quantify any protein or set of proteins present in a biological system. However, because typical biological samples contain a complex mixture of proteins and other components, analysis of such samples using mass spectrometry is not straightforward.

Certain tandem mass spectrometry ("MS/MS") systems have been developed to detect proteins in biological samples. In this approach, the sample is extracted to recover the proteins, optionally through the use of fractionation by chromatography or SDS-PAGE or other separation techniques. The protein fractions are subjected to proteolytic digestion to obtain component peptides, which are desalted and concentrated. The resulting peptide mixture is subjected to an initial mass spectrometry analysis, designated MS1. The MS1 spectrum depicts the intensity of signal, which corresponds to the amount of the peptide present in the sample. Ions of interest in the MS1 spectrum are selected and subjected to a second mass spectrometry event, induced by collision-induced dissociation (CID), which results in fragmentation of the selected peptide to yield a second mass spectrum (MS2) with sufficient information to permit identification of the peptide by comparison to available databases. However, because such MS/MS analysis systems are limited by the ability of the instrument to detect a peptide of interest in the MS1 spectrum, only proteins of relatively high abundance are detected. Furthermore, even if a particular protein is identified, the intensity of a particular m/z ratio in an MS1 spectrum does not permit quantitation absent some internal standard.

The quantitation issue has been addressed in alternative systems through the addition an internal standard having a known m/z relationship with the protein or peptide of interest. Quantitation is achieved by comparing the relative intensities of the internal standard, which is added to the sample in a known amount, and the target protein or peptide. Alternatively, relative amounts of proteins in mixtures can be determined by comparing the relative intensities of peptides derived from two different samples.

Currently, "shotgun" mass spectrometry (MS), paired with stable isotope labeling of proteins or peptides, is an attractive and widely applied approach for quantitative proteomics. A variety of methods for the incorporation of stable isotope labels into proteins have been reported, and include metabolic labeling (e.g., stable isotope labeling with amino acids in cell culture, or "SILAC"), chemical derivation of proteins (e.g., isotope coded affinity tag, or "ICAT") or peptides (e.g., isobaric tag for relative and absolute quantitation ("iTRAQ"), tandem mass tag technology ("TMT"), isotope coded protein labeling ("ICPL")), and enzymatic labeling of peptides. See, e.g., Colzani, M. et al., *Mol. Cell. Proteomics* (2008) 7.5:927-937; Hanke, S. et al., *J. Proteome Res.* (2008) 7:1118-1130; Thompson, A. et al., *Anal. Chem.* (2003) 75:1895-1904; Ross, P. L. et al., *Mol. Cell. Proteom.* (2004) 3:1154-1169. A review of various mass spectrometry-based analytical platforms is provided by Doman, B., et al., *Science* (2006) 312: 212-217.

In the SILAC approach, the internal standard is a peptide identical to the peptide of interest, which has been modified with specific isotopic substitutions that alter its m/z ratio but not its chromatographic or chemical behavior. For example, the internal standard is generally a heavy isotopic form of the desired protein (i.e., containing rarer, heavier isotopes such as $^{15}N$, $^{18}O$, and/or $^{13}C$). The heavy standard is added to the initial extract and is carried along with the peptides or proteins of interest through the sample preparation and analysis process. The peak generated in MS1 for the peptide of interest is compared to the corresponding peak for the heavy internal standard to quantify the target peptide. In similar methods, samples are spiked with heavy isotopes at later points in the sample preparation process; for example, QconCAT uses concatenated peptides, and the AQUA® method includes peptide standards and $H_2^{18}O$-digestion of protein standards. Alternatively, the relative amounts of proteins in mixture can be determined by differentially labeling the proteins with stable isotopes. Colzani et al. describe a more complex form of the SILAC method involving two isobaric forms of the heavy protein.

While such shotgun MS-based quantitative proteomics platforms have been used to quantify significant fractions of proteomes, the sensitivity, accuracy or quantitation, and reproducibility of the approaches do not meet the demands of many proteomics studies. To address these issues, recent efforts have focused on developing MS-based methods to monitor specific sets of proteins. Such proteomics platforms are expected to play important roles in clinical applications as well as in basic science studies where sets of proteins need to be consistently quantified under different conditions. One particularly promising targeted approach involves the use of selected or multiple reaction monitoring ("SRM" or "MRM") mass spectrometry of specific sets of parent and fragment ions (transitions) for each targeted peptide using triple quadrupole (QQQ) instruments. Other related methods involve the use of inclusion lists with high mass accuracy scanning mass spectrometers, such as the LTQ Orbitrap, to focus MS analysis on predetermined precursor ions.

However, these advanced methods still face limitations. For instance, although inclusion list methods can provide enhanced sensitivity and reproducibility, the target precursor ion must still be detectable in an MS1 survey scan for a fragment ion spectrum (MS2 or MS/MS) to be generated. This problem becomes critical when the targeted peptides are of low abundance in biological samples with high complexity and dynamic range. The SRM method is a sensitive, reproducible, and quantitative targeted approach, but its application is limited by a prerequisite assay optimization process. Such optimization typically involves selecting the most suitable transitions for each targeted peptide, and determining optimal collision energy settings and liquid chromatography (LC) retention time characteristics for each target peptide. In addition, quantification is typically determined based on a limited number of transitions per peptide made on QQQ instruments with modest mass accuracy and resolution; thus, the accuracy of the measurement may be compromised by chemical noise and co-eluting ions, especially in complex samples.

Existing reporter ion-based isobaric tagging reagents (e.g., iTRAQ or TMT) used for MS2-based quantification are limited by: (1) the need to detect reporter ions in the low mass range, which limits the range of suitable instruments; and (2) potential interference by co-eluting peptide ions with similar m/z values.

Other MS2-based quantitative proteomics approach have been described that use peptide-specific fragment ions for quantification. However, in these approaches an enlarged precursor isolation window (e.g., 10 m/z units) is needed to cover the m/z range of both light and heavy isotopically labeled precursor peptides for simultaneous CID and subsequent quantification (based on y-ions). While the use of multiple fragment ions for quantification improves accuracy, this advantage is muted by the inclusion in the broad window of unrelated peptide ions and chemical noise in the collision cell which may interfere with quantification.

Koehler et al. reported an approach for quantifying isobaric peptides during MS2. Koehler, C. J. et al., *J. Proteome Res.* 2009, 8(9), 4333-41. In that study, the isobaric peptides were generated by chemical labeling of LysC digested peptides with both succinic anhydride ($\Delta 0$ or $\Delta 4$) at the N-termini and 2-methoxy-4,5-dihydro-1H-imidazole ($\Delta 4$ or $\Delta 0$) at the C-terminal lysine residues, respectively. Although the isotopically labeled isobaric peptides proved useful for quantification, the approach is restricted to peptides ending with lysine and requires two amine-based labeling steps. Most importantly, protein abundance is only semi-quantitatively estimated from Mascot scores rather than from direct measurement of fragment ion intensities.

Thus, although there are a variety of available strategies for effecting identification and quantitation of proteins and peptides in complex samples, there remains a need for a proteomics platform which efficiently identifies subject peptides and proteins, and/or generates reproducible and accurate quantitative measurements in a high throughput manner, even at low target concentrations.

SUMMARY OF THE INVENTION

In one aspect, the present invention relates to an MS2-based ion quantitation ("MSTIQ") method for quantifying peptides of interest. In this method, a peptide of interest is modified at one terminus (the C- or N-terminus) with a first tag which contains heavy isotopes ("heavy"), and at the other terminus with an isotopically "light" second tag. An internal standard, or "MSTIQ standard peptide," is prepared as an isobaric analog to the modified peptide of interest. The internal standard is identical to the modified peptide of interest in terms of its sequence (such that it behaves identically to the modified peptide of interest during synthetic reactions, sample work-up, chromatography, and extraction methods), but has heavy and light tags at opposite termini in each case; the difference in m/z ($\Delta$m/z) between the isotopically heavy tag at the C-terminus of isobaric pair member 1 and the corresponding light tag at the C-terminus of isobaric pair member 2 is balanced by the same $\Delta$m/z between the isotopically heavy tag at the N-terminus of isobaric pair member 2 and the corresponding light tag at the N-terminus of isobaric pair member 1. Herein, the members of such an isobaric peptide pair are also referred to as "light-heavy" ("LH") and "heavy-light" ("HL") peptides. The internal standard is spiked at a known concentration into the sample containing the modified peptide of interest, and the mixture is analyzed by tandem mass spectrometry.

In the first MS phase ("MS1"), the isobaric pair appears as a single m/z peak; the instrument essentially detects the parent ions for both members of the isobaric pair at the same m/z. These parent ions are selected for MS2 analysis by CID fragmentation. CID generates multiple pairs of sequence-specific fragment ions (e.g., b- and y-ions) corresponding to the N-terminal and C-terminal fragments of each isobaric peptide, with a mass difference for each pair equal the mass difference between the heavy and light isotopic tags in the pair. The relative amount of the modified peptide of interest and the internal standard is determined from the ratios of the intensities of the ions in the fragment ion pairs, as each fragment pair consists of a fragment ion from each isobaric pair member. The fragmentation pattern is also used to identify the sequence of the peptide of interest, as each peptide can fragment along the peptide backbone and produce corresponding fragment ions. See FIG. 1 for a schematic overview of this method.

Thus, the invention is directed to a method of quantifying a peptide of interest in a sample comprising: (a) modifying the peptide of interest at terminus (1) with an isotopically heavy first tag (A*) and at terminus (2) with an isotopically light second tag (B) to form a structure of Formula (I):

(b) adding an internal standard to the sample, wherein the internal standard comprises the sequence of the peptide of interest modified at terminus (1) with an isotopically light variant of the first tag (A) and at terminus (2) with an isotopically heavy variant of the second tag (B*), to form a structure of Formula (II):

wherein the difference in mass between (A*) and (A) is equal to the difference in mass between (B*) and (B) such that the internal standard is isobaric to the modified peptide of interest; (c) obtaining a first mass spectrum of the sample; (d) identifying the ion in the first mass spectrum which corresponds to both the modified peptide of interest and the internal standard; (e) obtaining a second mass spectrum by CID fragmentation of the ions of both the modified peptide of interest and the internal standard identified in step (d); (f) comparing the relative intensities of fragment ions of the modified peptide of interest and fragment ions of the internal standard; and (g) quantifying the peptide of interest based no the comparison from step (f).

In another aspect, the invention is directed to an Index-ion Triggered Analysis ("ITA") method of detecting a peptide of interest in a sample. In this method, the sample containing a modified peptide of interest is spiked with an index peptide, which is an isotopically different form of the modified peptide of interest (lighter or heavier than the modified peptide of interest), in an amount sufficient to ensure detection of the index peptide parent ion during MS1 analysis. As an isotopic variant of the modified peptide of interest, the index peptide behaves identically to the modified peptide of interest during chemical synthesis, sample work-up, chromatography, and extraction methods. The spiked sample mixture is analyzed by tandem mass spectrometry. The parent ion of the index peptide appears at a known Δm/z from that of the peptide of interest in MS1. Upon MS1 detection of the index peptide parent ion, the abundance of which is under experimental control, the MS instrument is programmed to acquire MS2 spectra at plus or minus Δm/z from the detected index peptide (the difference in the expected m/z of the parent ion of the modified peptide of interest and the expected m/z of the index peptide parent ion), independent of the concentration of the modified peptide of interest in the sample or the intensity of its MS1 parent ion. Generally, the MS instrument is programmed to acquire MS2 spectra for a narrow range of m/z units (the "CID isolation window") around the m/z of the modified peptide of interest. From an analysis of the MS2 fragmentation pattern, the presence or absence of the peptide of interest in the sample is determined.

Thus, the invention is directed to a method of detecting a peptide of interest in a sample comprising: (a) modifying the peptide of interest at terminus (1) with a first tag (X) and at terminus (2) with a second tag (Y) to form a structure of Formula (III):

X-Peptide-Y (III);

(b) adding an index peptide to the sample, wherein the index peptide comprises the sequence of the peptide of interest, modified at terminus (1) with a first tag (X*) and at terminus (2) with a second tag (Y*), to form a structure of Formula (IV):

X*-Peptide-Y* (IV), wherein each of (X), (X*), (Y), and (Y*) is independently isotopically normal or comprises at least one heavy atom isotope, and wherein the difference, x, between the m/z of the index peptide parent ion and the m/z for the parent ion for the peptide of interest is large enough that isotopic peaks of the index peptide parent ion fall outside an eight m/z unit or smaller CID isolation window around the m/z of the parent ion for the peptide of interest; (c) obtaining a first mass spectrum of the sample; (d) detecting the ion for the index peptide in the first mass spectrum; (e) obtaining a second mass spectrum by CID fragmentation at a position x Daltons from the index peptide ion; and (f) analyzing the second mass spectrum for fragment ions indicative of the peptide of interest.

The invention further contemplates a method which combines both the ITA and MSTIQ protocols (the "iMSTIQ" method) to allow detection, identification, and quantification of a peptide of interest. See FIG. 2. In this aspect, the invention is directed to a method of analyzing a peptide of interest in a sample comprising: (a) modifying the peptide of interest at terminus (1) with an isotopically heavy first tag (C*) and at terminus (2) with an isotopically light second tag (D) to form a structure of Formula (V):

C*-Peptide-D (V);

(b) adding an internal standard to the sample, wherein the internal standard comprises the sequence of the peptide of interest modified at terminus (1) with an isotopically light variant of the first tag (C) and at terminus (2) with an isotopically heavy variant of the second tag (D*), to form a structure of Formula (VI):

C-Peptide-D* (VI), wherein the difference in mass between C* and C is equal to the difference in mass between D* and D such that the internal standard is isobaric to the modified peptide of interest; (c) adding an index peptide to the sample, wherein the index peptide comprises the sequence of the peptide of interest, (I) modified at terminus (1) with an isotopically heavy tag (C*) and at terminus (2) with an isotopically heavy tag (D*) to form a structure of Formula (VII):

C*-Peptide-D* (VII); or (II) modified at terminus (1) with the isotopically light tag (C) and at terminus (2) with the isotopically light tag (D) to form a structure of Formula (VIII):

C-Peptide-D (VIII);

and wherein the difference, x, between the m/z of the index peptide parent ion and the m/z for the parent ion for the peptide of interest is large enough that isotopic peaks of the index peptide parent ion fall outside an eight m/z unit or less CID isolation window around the m/z of the parent ion for the peptide of interest; (e) detecting the ion in the first mass spectrum which corresponds to the index peptide; (f) obtaining a second mass spectrum by CID fragmentation at x m/z units less than the m/z for the index peptide parent ion; (g) analyzing the second mass spectrum for fragment ions indicative of the modified peptide of interest; (h) comparing the relative intensities of fragment ions of the modified peptide of interest and fragment ions of the internal standard; and (i) quantifying the peptide of interest based no the comparison from step (h).

BRIEF DESCRIPTION OF THE DRAWINGS

FIG. 5. Quantification of peptides in Example 7a. FIG. 5 shows the correlation between the expected ratio (log 10) of the target peptide to the MSTIQ internal standard peptide.

FIGS. 8 A-C. Results of Example 8. Absolute abundance (y-axis) of 14 detected peptides in all six samples is plotted as a function of time points (x-axis). Data from the control sample are shown at the 19 h time point for clarity. (A) Plots for the three non-specific peptides (Group 2 in Table 1). (B) Plots for the eight targeted peptides that displayed LPS-dependent release. (C) Plots for three targeted peptides that did not display LPS-dependent release.

DETAILED DESCRIPTION OF THE INVENTION

Figure 1:
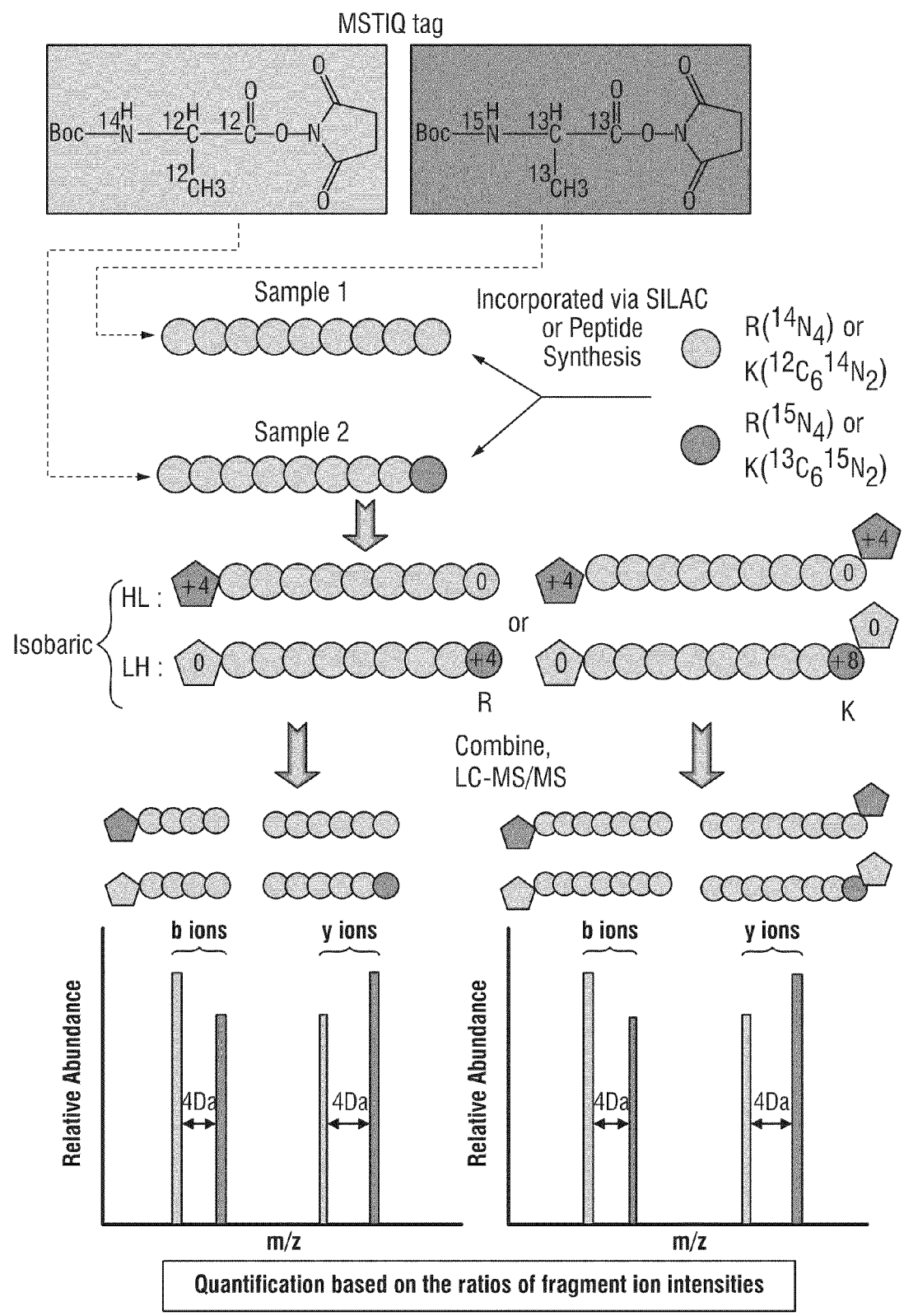
FIG. 1. Schematic overview of an exemplary embodiment of the MSTIQ quantification strategy. Peptide Sample 1, derived from the test protein sample, and Peptide Sample 2, which is purchased commercially, prepared by peptide synthesis, or both, are isotopically labeled at their C-termini with either light (arginine and lysine; white circles) or heavy ($^{15}N_4$-arginine or $^{13}C_6^{15}N_2$-lysine; black circles) amino acids. The light and heavy peptides are then treated with isotopically heavy (black pentagons) or light (white pentagons) amine labeling reagents, respectively, to produce isobaric HL and LH peptides. The structures of exemplary MSTIQ amine labeling reagents are shown. The peptides are combined and subjected to LC-MS/MS analysis. After CID in MS2, multiple pairs of sequence-specific fragment ions (e.g., b- and y-ions) are produced which have a mass difference of 4 Da. The relative abundance of the peptides in the two samples is determined from the ratios of the intensities of corresponding fragment ion pairs.
Figure 2:
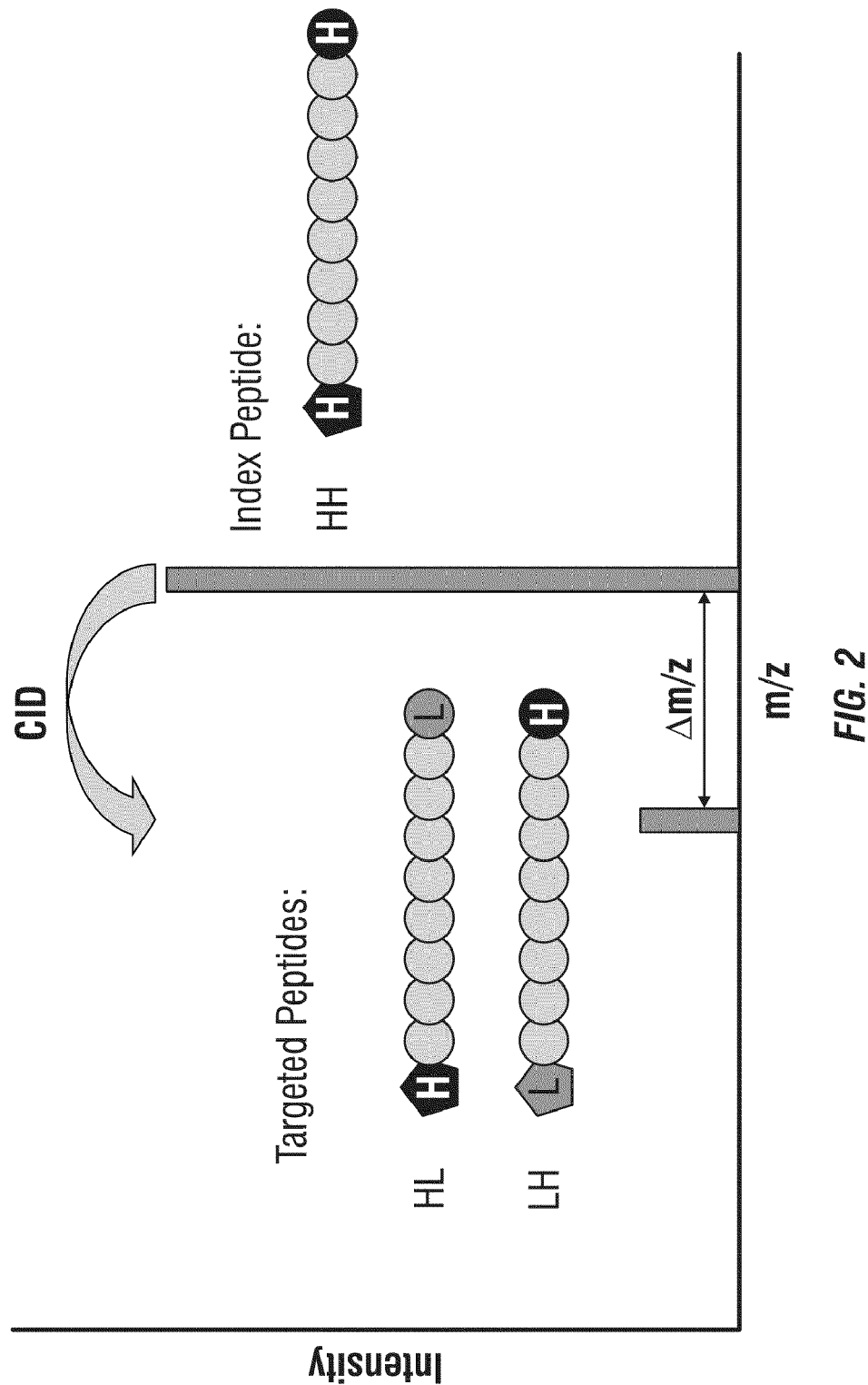
FIG. 2. Schematic overview of the MS1 phase of the iMSTIQ strategy. Detection of an index peptide ("HH") spiked into the peptide sample triggers CID on the predicted m/z for the modified peptide of interest. Parent ions for the modified peptide of interest and the internal standard ("HL" and "LH" peptides), which each contain one isotopically heavy tag and one isotopically light tag at their termini, both occur at the same m/z.

The term "tag" refers to an amino acid or other appropriate peptide-modifying chemical tag, or a combination thereof. For example, a tag may comprise a single amino acid, two amino acids, a non-amino acid chemical tag, or an amino acid further modified with a non-amino acid chemical tag. A tag may be or may include part of the sequence of the peptide of interest, e.g., may be or may include the actual C- or N-terminal residue of the peptide of interest, optionally appended with a second amino acid or a chemical tag, or the tag may be appended to the sequence of the peptide of interest. Where a tag is appended to the sequence of the peptide of interest, it is appended the C- or N-terminus of the sequence of the peptide of interest. An isotopically heavy tag comprises at least one atom isotope with a greater mass number than its naturally most abundant counterpart ("heavy atom isotope"), e.g., $^{13}C$ in place of $^{12}C$. The heavy atom isotope has a greater mass number, but the same atomic number, as its naturally most abundant counterpart. As is relevant for mass spectrometry methods, modification of a compound with an isotopically heavy tag yields a compound with a greater m/z than the m/z for the natural isotopic form of the same compound. An isotopically light variant of a tag has fewer heavy atom isotopes than the isotopically heavy analog of the same tag. An isotopically "light" tag may be an isotopically normal tag (the naturally most abundant form). Thus, the terms "heavy" and "light" are relative terms. Preferably, isotopically heavy or light tags incorporate stable atom isotopes.

The term "isobar" can be defined as one of two or more atoms with a common mass number but different atomic numbers. Isobars possess approximately equal masses, but differ in their exact masses. "Isobaric peptides" are peptides with the same mass, but labeled differently by the use of stable isotopes at the N- and C-termini. In such an "isobaric" pair, the peptides have the same mass number (thus roughly the same mass), and any increase in isotopic content (atomic number) of one member of the pair is balanced by the same increase in isotopic content in the other member of the pair. For example, a peptide of interest may be modified at its N-terminus with a heavy tag and the C-terminus with an isotopically normal tag. An internal standard peptide which is isobaric to the modified peptide of interest is modified isotopically in the opposite direction.

Suitable N-terminal tags include any chemical moiety which may be covalently bound to the N-terminus of a peptide. Preferred N-terminal tags are amino acids, such as alanine, other amine reactive chemical tags such as those derived from mTRAQ® reagents (available from Applied Biosystems, located on the World Wide Web at appliedbiosystems.com/cms/groups/psm_support/documents/generaldocuments/cms_054141.pdf), or isotopically heavy variants thereof. Particularly preferred N-terminal tags are alanine, ($^{13}C_3{}^{15}N$)-alanine (all three alanine carbons labeled with $^{13}C$; alanine nitrogen labeled with $^{15}N$), or light or heavy mTRAQ® reagents.

N-terminal tags may be incorporated into or appended to the sequence of interest by, for example, chemical reaction of a suitable tagging reagent, such as an activated ester form of an amino acid, or other amine-reactive tagging reagent, with the N-terminus of the peptide of interest.

Suitable C-terminal tags include any chemical moiety which may be covalently bound to the C-terminus of a peptide. In preferred embodiments, C-terminal tags are amino acids which are revealed as C-terminal residues following proteolytic digestion of a protein sample. For example, digestion with trypsin generally cleaves proteins to give peptides with lysine or arginine residues at the C-termini. Other proteolytic agents will cleave proteins at different locations to yield peptides with different terminal amino acids. Preferred C-terminal tags are lysine, ($^{13}C_6{}^{15}N_2$)-lysine (all six lysine carbons replaced with $^{13}C$, and both lysine nitrogens replaced with $^{15}N$), arginine, or $^{15}N_4$-arginine (all four arginine nitrogens replaced with $^{15}N$).

C-terminal tags may be incorporated into or appended to the sequence of interest by, for example: 1) metabolic labeling with an isotopically heavy or light amino acid; 2) chemical synthesis with an isotopically heavy or light tag; or 3) where the C-terminal residue of the peptide of interest is arginine, trypsinolysis of the protein sample in the presence of isotopically light or heavy water, e.g., $H_2{}^{18}O$.

Where the peptide of interest contains or is appended with a C-terminal lysine or ($^{13}C_6^{15}N_2$)-lysine, certain N-terminal tagging reagents will react with both the N-terminus of the peptide and with the sidechain amino group of the lysine. One skilled in the art will recognize the appendage of such modifications will necessitate similar modifications to the other peptides in the analysis system in order to balance the isotopic distribution as desired. Thus, in some embodiments, preferred C-terminal tags are lysine or ($^{13}C_6^{15}N_2$)-lysine tags each substituted at the sidechain amino group with alanine or ($^{13}C_3^{15}N$)-alanine. Further preferred C-terminal tags are lysine-($^{13}C_3^{15}N$)-alanine, ($^{13}C_6^{15}N_2$)-lysine-alanine, or ($^{13}C_6^{15}N_2$)-lysine-($^{13}C_3^{15}N$)-alanine. Alternatively, preferred C-terminal tags are lysine-*mTRAQ (*mTRAQ=heavy variant of mTRAQ tag), ($^{13}C_6^{15}N_2$)-lysine-mTRAQ, or ($^{13}C_6^{15}N_2$)-lysine-*mTRAQ. The terms lysine-alanine and lysine-mTRAQ, and the "heavy" variants thereof, are defined as having the alanine or mTRAQ moieties bound to the lysine sidechain amine.

In preferred embodiments of the invention, first and second mass spectra are obtained on an instrument with high mass accuracy, resolution, and throughput. In further preferred embodiments, first and second mass spectra are obtained on a LTQ Orbitrap instrument.

In preferred embodiments, the CID isolation window is less than 8 m/z units. In further preferred embodiments, the CID isolation window is less than 3 m/z units. In still further preferred embodiments, the CID isolation window is between 1 and 3 m/z units.

MSTIQ Method:

In preferred embodiments of the MSTIQ method, terminus (1) of each peptide is its C-terminus and terminus (2) of each peptide is its N-terminus. In other preferred embodiments, terminus (1) of each peptide is its N-terminus and terminus (2) of each peptide is its C-terminus.

One of skill in the art will recognize that (A), (A*), (B), and (B*) may be any suitable chemical tag, each of which may contain zero or more heavy atom isotopes, so long as the resulting modified peptide of interest and the internal standard are isobaric.

In preferred embodiments, terminus (1) of each peptide is its C-terminus, (A) and (A*) are each independently lysine, lysine-alanine, lysine-mTRAQ, or arginine, or any isotopically labeled variant thereof, and (B) and (B*) are each independently alanine or mTRAQ, or any isotopically labeled variant thereof. In preferred embodiments, terminus (1) of each peptide is its C-terminus, (A) is lysine, lysine-alanine, lysine-($^{13}C_3^{15}N$)-alanine, $^{13}C_6^{15}N_2$-lysine-alanine, lysine-mTRAQ, lysine-*mTRAQ, $^{13}C_6^{15}N_2$-lysine-mTRAQ, or arginine, and (A*) is $^{13}C_6^{15}N_2$-lysine, $^{13}C_6^{15}N_2$-lysine-alanine, $^{13}C_6^{15}N_2$-lysine-($^{13}C_3^{15}N$)-alanine, $^{13}C_6^{15}N_2$-lysine-mTRAQ, $^{13}C_6^{15}N_2$-lysine-*mTRAQ, or $^{15}N_4$-arginine. In further preferred embodiments, terminus (1) of each peptide is its C-terminus, terminus (2) of each peptide is its N-terminus, (A) is lysine, lysine-alanine, lysine-($^{13}C_3^{15}N$)-alanine, $^{13}C_6^{15}N_2$-lysine-alanine, lysine-mTRAQ, lysine-*mTRAQ, $^{13}C_6^{15}N_2$-lysine-mTRAQ, or arginine, (A*) is $^{13}C_6^{15}N_2$-lysine, $^{13}C_6^{15}N_2$-lysine-alanine, $^{13}C_6^{15}N_2$-lysine-($^{13}C_3^{15}N$)-alanine, $^{13}C_6^{15}N_2$-lysine-mTRAQ, $^{13}C_6^{15}N_2$-lysine-*mTRAQ, or $^{15}N_4$-arginine, (B*) is ($^{13}C_3^{15}N$)-alanine or is derived from an isotopically heavy mTRAQ reagent, and (B) is alanine or an isotopically light variant of the mTRAQ reagent. In still further preferred embodiments, terminus (1) of each peptide is its C-terminus, (A) is lysine-($^{13}C_3^{15}N$)-alanine, (A*) is $^{13}C_6^{15}N_2$-lysine-alanine, (B) is alanine, and (B*) is ($^{13}C_3^{15}N$)-alanine.

In preferred embodiments, terminus (1) of each peptide is its N-terminus, (B) and (B*) are each independently lysine, lysine-alanine, lysine-mTRAQ, or arginine, or any isotopically labeled variant thereof, and (A) and (A*) are each independently alanine or mTRAQ, or any isotopically labeled variant thereof. In preferred embodiments, terminus (1) of each peptide is its N-terminus, (A*) is ($^{13}C_3^{15}N$)-alanine or is derived from an isotopically heavy mTRAQ reagent, and (A) is alanine or an isotopically light variant of the mTRAQ reagent. In still further preferred embodiments, terminus (1) of each peptide is its N-terminus, (A*) is ($^{13}C_3^{15}N$)-alanine or is derived from an isotopically heavy mTRAQ reagent, (A) is alanine or an isotopically light variant of the mTRAQ reagent, terminus (2) of each peptide is its C-terminus, (B) is lysine, lysine-alanine, lysine-($^{13}C_3^{15}N$)-alanine, $^{13}C_6^{15}N_2$-lysine-alanine, lysine-mTRAQ, lysine-*mTRAQ, $^{13}C_6^{15}N_2$-lysine-mTRAQ, or arginine, and (B*) is $^{13}C_6^{15}N_2$-lysine, $^{13}C_6^{15}N_2$-lysine-alanine, $^{13}C_6^{15}N_2$-lysine-($^{13}C_3^{15}N$)-alanine, $^{13}C_6^{15}N_2$-lysine-mTRAQ, $^{13}C_6^{15}N_2$-lysine-*mTRAQ, or $^{15}N_4$-arginine. In still further preferred embodiments, terminus (1) of each peptide is its N-terminus, (A) is alanine, (A*) is ($^{13}C_3^{15}N$)-alanine, terminus (2) of each peptide is its C-terminus, (B) is lysine-($^{13}C_3^{15}N$)-alanine, and (B*) is $^{13}C_6^{15}N_2$-lysine-alanine.

ITA Method:

In preferred embodiments of the ITA method, terminus (1) of each peptide is its C-terminus and terminus (2) of each peptide is its N-terminus. In other preferred embodiments, terminus (1) of each peptide is its N-terminus and terminus (2) of each peptide is its C-terminus.

One of skill in the art will recognize that (X), (X*), (Y), and (Y*) may be any suitable chemical tag, each of which may contain zero or more heavy atom isotopes.

In some embodiments, both (X) and (Y) are isotopically light. In embodiments where both (X) and (Y) are isotopically light, (X*) and (Y*) are preferably both isotopically heavy. In embodiments where both (X) and (Y) have no heavy atom isotopes and the tags are part of the sequence of the peptide of interest, one skilled in the art will recognize the structure X-Peptide-Y is chemically and isotopically identical to the structure of the peptide of interest.

In other preferred embodiments of the ITA method, the peptide of interest is modified at one terminus (the C- or N-terminus) with an isotopically heavy first tag ("heavy"), and at the other terminus with an isotopically light second tag ("light"), as described for the MSTIQ method, above. The index peptide is identical in sequence to the modified peptide of interest, but both tags are "heavy" or "light" variants. Herein, such preferred index peptides are also referred to as "heavy-heavy" ("HH") peptides. In further preferred embodiments, one of (X) and (Y) is isotopically light and the other is isotopically heavy, and (X*) and (Y*) are either both isotopically light or are both isotopically heavy. Preferably, (X*) and "Y*" are both isotopically heavy.

Thus, in preferred embodiments, terminus (1) of each peptide is its C-terminus, (X) is lysine, lysine-alanine, $^{13}C_6^{15}N_2$-lysine-alanine, lysine-($^{13}C_3^{15}N$)-alanine, lysine-mTRAQ, $^{13}C_6^{15}N_2$-lysine-mTRAQ, lysine-*mTRAQ, or arginine, and (X*) is $^{13}C_6^{15}N_2$-lysine, $^{13}C_6^{15}N_2$-lysine-alanine, $^{13}C_6^{15}N_2$-lysine-($^{13}C_3^{15}N$)-alanine, $^{13}C_6^{15}N_2$-lysine-mTRAQ, $^{13}C_6^{15}N_2$-lysine-*mTRAQ, or $^{15}N_4$-arginine. In further preferred embodiments, terminus (1) of each peptide is its C-terminus, terminus (2) of each peptide is its N-terminus, (X) is lysine, lysine-alanine, $^{13}C_6^{15}N_2$-lysine-alanine, lysine-($^{13}C_3^{15}N$)-alanine, lysine-mTRAQ, $^{13}C_6^{15}N_2$-lysine-mTRAQ, lysine-*mTRAQ, or arginine, (Y) is alanine or an isotopically light variant of the mTRAQ reagent, (X*) is $^{13}C_6{}^{15}N_2$-lysine, $^{13}C_6{}^{15}N_2$-lysine-alanine, $^{13}C_6{}^{15}N_2$-lysine-($^{13}C_3{}^{15}N$)-alanine, $^{13}C_6{}^{15}N_2$-lysine-mTRAQ, $^{13}C_6{}^{15}N_2$-lysine-*mTRAQ, or $^{15}N_4$-arginine, and (Y*) is ($^{13}C_3{}^{15}N$)-alanine or is derived from an isotopically heavy mTRAQ reagent. In still further preferred embodiments, terminus (1) of each peptide is its C-terminus, terminus (2) of each peptide is its N-terminus, (X) is $^{13}C_6{}^{15}N_2$-lysine-alanine or lysine-($^{13}C_3{}^{15}N$)-alanine, (Y) is alanine, (X*) is $^{13}C_6{}^{15}N_2$-lysine-($^{13}C_3{}^{15}N$)-alanine, and (Y*) is ($^{13}C_3{}^{15}N$)-alanine.

In preferred embodiments, terminus (1) of each peptide is its N-terminus, (X*) is ($^{13}C_3{}^{15}N$)-alanine or is derived from an isotopically heavy mTRAQ reagent, and (X) is alanine or an isotopically light variant of the mTRAQ reagent. In still further preferred embodiments, terminus (1) of each peptide is its N-terminus, (X*) is ($^{13}C_3{}^{15}N$)-alanine or is derived from an isotopically heavy mTRAQ reagent, (X) is alanine or an isotopically light variant of the mTRAQ reagent, terminus (2) of each peptide is its C-terminus, (Y*) is $^{13}C_6{}^{15}N_2$-lysine, $^{13}C_6{}^{15}N_2$-lysine-alanine, $^{13}C_6{}^{15}N_2$-lysine-($^{13}C_3{}^{15}N$)-alanine, $^{13}C_6{}^{15}N_2$-lysine-mTRAQ, $^{13}C_6{}^{15}N_2$-lysine-*mTRAQ, or $^{15}N_4$-arginine, and (Y) is lysine, lysine-alanine, $^{13}C_6{}^{15}N_2$-lysine-alanine, lysine-($^{13}C_3{}^{15}N$)-alanine, lysine-mTRAQ, $^{13}C_6{}^{15}N_2$-lysine-mTRAQ, lysine-*mTRAQ, or arginine. In still further preferred embodiments, terminus (1) of each peptide is its N-terminus, (X*) is ($^{13}C_3{}^{15}N$)-alanine, (X) is alanine, terminus (2) of each peptide is its C-terminus, (Y*) is $^{13}C_6{}^{15}N_2$-lysine-($^{13}C_3{}^{15}N$)-alanine, and (Y) is $^{13}C_6{}^{15}N_2$-lysine-alanine or lysine-($^{13}C_3{}^{15}N$)-alanine.

In preferred embodiments, x is greater than or equal to +3 Daltons, or is less than or equal to −6 Daltons.

In further embodiments, step (e) further comprises obtaining a second mass spectrum by CID fragmentation of the index peptide ion.

iMSTIQ Method:

In some embodiments, terminus (1) of each peptide is its C-terminus and terminus (2) of each peptide is its N-terminus. In other embodiments, terminus (1) of each peptide is its N-terminus and terminus (2) of each peptide is its C-terminus.

One of skill in the art will recognize that (C), (C*), (D), and (D*) may be any suitable chemical tag, each of which may contain zero or more heavy atom isotopes, so long as the resulting modified peptide of interest and the internal standard are isobaric.

In some embodiments of the iMSTIQ method, tags (C*) and (D*) in Formula (VII) may be isotopically heavier than the heavy chemical tags (C*) and (D*) in Formulae (V) and (VI). In other words, while all (C)- or (D)-type tags are isotopically identical, the heavy (C*) and (D*) tags in the index peptide may be of greater isotopic content than those in the modified peptide of interest or the internal standard peptide.

In preferred embodiments of the iMSTIQ method, terminus (1) of each peptide is its C-terminus and terminus (2) of each peptide is its N-terminus.

In preferred embodiments, terminus (1) of each peptide is its C-terminus, (C) and (C*) are each independently lysine, lysine-alanine, lysine-mTRAQ, or arginine, or any isotopically labeled variant thereof, and (D) and (D*) are each independently alanine or mTRAQ, or any isotopically labeled variant thereof. In further preferred embodiments, terminus (1) of each peptide is its C-terminus, (C) is lysine, lysine-alanine, $^{13}C_6{}^{15}N_2$-lysine-alanine, lysine-($^{13}C_3{}^{15}N$)-alanine, lysine-mTRAQ, $^{13}C_6{}^{15}N_2$-lysine-mTRAQ, lysine-*mTRAQ, or arginine, and (C*) is $^{13}C_6{}^{15}N_2$-lysine, $^{13}C_6{}^{15}N_2$-lysine-alanine, $^{13}C_6{}^{15}N_2$-lysine-($^{13}C_3{}^{15}N$)-alanine, $^{13}C_6{}^{15}N_2$-lysine-mTRAQ, $^{13}C_6{}^{15}N_2$-lysine-*mTRAQ, or $^{15}N_4$-arginine. In further preferred embodiments, terminus (1) of each peptide is its C-terminus, terminus (2) of each peptide is its N-terminus, (C) is lysine, lysine-alanine, $^{13}C_6{}^{15}N_2$-lysine-alanine, lysine-($^{13}C_3{}^{15}N$)-alanine, lysine-mTRAQ, $^{13}C_6{}^{15}N_2$-lysine-mTRAQ, lysine-*mTRAQ, or arginine, (C*) is $^{13}C_6{}^{15}N_2$-lysine, $^{13}C_6{}^{15}N_2$-lysine-alanine, $^{13}C_6{}^{15}N_2$-lysine-($^{13}C_3{}^{15}N$)-alanine, $^{13}C_6{}^{15}N_2$-lysine-mTRAQ, $^{13}C_6{}^{15}N_2$-lysine-*mTRAQ, or $^{15}N_4$-arginine, (D*) is ($^{13}C_3{}^{15}N$)-alanine or is derived from an isotopically heavy mTRAQ reagent, and (D) is alanine or an isotopically light variant of the mTRAQ reagent. In still further preferred embodiments, terminus (1) of each peptide is its C-terminus, terminus (2) of each peptide is its N-terminus, (C) is lysine-($^{13}C_3{}^{15}N$)-alanine, (D) is alanine, (C*) in Formula (V) is $^{13}C_6{}^{15}N_2$-lysine-alanine, (C*) in Formula (VII) is $^{13}C_6{}^{15}N_2$-lysine-($^{13}C_3{}^{15}N$)-alanine, and (D*) is ($^{13}C_3{}^{15}N$)-alanine.

In preferred embodiments, terminus (1) of each peptide is its N-terminus, (D) and (D*) are each independently lysine, lysine-alanine, lysine-mTRAQ, or arginine, or any isotopically labeled variant thereof, and (C) and (C*) are each independently alanine or mTRAQ, or any isotopically labeled variant thereof. In preferred embodiments, terminus (1) of each peptide is its N-terminus, (C*) is ($^{13}C_3{}^{15}N$)-alanine or is derived from an isotopically heavy mTRAQ reagent, and (C) is alanine or an isotopically light variant of the mTRAQ reagent. In still further preferred embodiments, terminus (1) of each peptide is its N-terminus, (C*) is ($^{13}C_3{}^{15}N$)-alanine or is derived from an isotopically heavy mTRAQ reagent, (C) is alanine or an isotopically light variant of the mTRAQ reagent, terminus (2) of each peptide is its C-terminus, (D*) is $^{13}C_6{}^{15}N_2$-lysine, $^{13}C_6{}^{15}N_2$-lysine-alanine, $^{13}C_6{}^{15}N_2$-lysine-($^{13}C_3{}^{15}N$)-alanine, $^{13}C_6{}^{15}N_2$-lysine-mTRAQ, $^{13}C_6{}^{15}N_2$-lysine-*mTRAQ, or $^{15}N_4$-arginine, and (D) is lysine, lysine-alanine, $^{13}C_6{}^{15}N_2$-lysine-alanine, lysine-($^{13}C_3{}^{15}N$)-alanine, lysine-mTRAQ, $^{13}C_6{}^{15}N_2$-lysine-mTRAQ, lysine-*mTRAQ, or arginine. In still further preferred embodiments, terminus (1) of each peptide is its N-terminus, (C*) is ($^{13}C_3{}^{15}N$)-alanine, (C) is alanine, terminus (2) of each peptide is its C-terminus, (D*) in Formula (VI) is $^{13}C_6{}^{15}N_2$-lysine-alanine, (D*) in Formula (VII) is $^{13}C_6{}^{15}N_2$-lysine-($^{13}C_3{}^{15}N$)-alanine, and (D) is lysine-($^{13}C_3{}^{15}N$)-alanine.

In further embodiments, step (f) of the iMSTIQ method further comprises obtaining a second mass spectrum by CID fragmentation of the index peptide ion.

General Methods:

Preparation of Isotopically Labeled Internal Standard and Index Peptides. Isotopically heavy peptides are commercially available, or are available by standard peptide synthesis methods using isotopically heavy or light tagging reagents. For example, to incorporate isotopically heavy labels at the N-termini, peptides may be reacted with isotopically heavy, activated amino acids, such as Boc-($^{13}C_3{}^{15}N$)-Ala)-OSu (See Example 1; "Su"=succinimidyl), or with heavy mTRAQ® reagents (Applied Biosystems, Foster City, Calif.). Isotopically light peptides are commercially available or are prepared by standard peptide synthesis methods.

Sample Preparation. Protein samples comprise individual proteins or mixtures of proteins, and may be derived from any appropriate source such as cell extracts, serum, or other bodily fluids. Proteins are typically digested with a suitable protease, such as trypsin, by standard methods to generate one or more peptides of interest, and the peptide mixture is desalted by $C_{18}$ chromatography.

Modification of Peptides of Interest. In an exemplary method for incorporating C-terminal tags, protein samples are grown in the presence of a suitable SILAC medium, such as SILAC-specific RPMI-1640 medium (Caisson Laboratories, North Logan, Utah)), containing isotopically heavy or light amino acids, such as lysine and arginine, or heavy variants thereof. The C-terminal tags may be incorporated before or after digestion of the protein samples. To incorporate N-terminal tags, digested peptide mixtures are suspended in a suitable buffer and treated with an N-terminal tagging reagent, such as a light or heavy activated amino acid ester or an mTRAQ® reagent. Any protecting groups on the tags are removed using standard deprotection methods. Samples are generally purified by $C_{18}$ chromatography.

Analysis by Liquid Chromatography-Mass Spectrometry. Known amounts of MSTIQ standard peptides and/or ITA index peptides are combined with the modified peptides of interest. Preferably, the internal standard is added at an amount equal to that of the modified peptide of interest. However, because quantitation is linear over a ~1000 fold range of concentration, concentrations across a broad range are effective. The index peptide is added at a level that will generate a strong signal during MS, preferably at approximately 50 times the noise level. The mixture is analyzed by nanoLC-MS/MS using an LTQ-Orbitrap™ instrument (Thermo Scientific) or it may be fractionated by strong cation exchange chromatography prior to LC-MS analysis.

Alternatively, peptide samples are analyzed by reversed phase HPLC (Agilent 1100 series) electro-spray ionization LC-MS using the LTQ Orbitrap. The HPLC column (75 µm×15 cm) is packed with $C_{18}$ resin (Magic $C_{18}$ AQ 5 µm, Michrom BioResources, Auburn, Calif.). Peptides are resolved by running a gradient of Buffer A (0.1% formic acid) to Buffer B (0.1% formic acid, 99.9% acetonitrile) as follows: 8-25% Buffer B over 34 min (for ITA experiments) or 53 min (for MSTIQ and iMSTIQ experiments); 25-35% Buffer B over six min (for ITA experiments) or 10 min (for MSTIQ and iMSTIQ experiments); 35-80% Buffer B over eight min (for ITA experiments) or 10 min (for MSTIQ and iMSTIQ experiments). A fixed flow rate of 350 nl/min is applied.

In general, MS1 scans are acquired by the Orbitrap with a resolution of 30,000 at 400 m/z. MS2 scans are acquired by the LTQ using normal scan mode except in the MSTIQ assay where MS2 scans are acquired by the Orbitrap with a resolution of 7,500 at 400 m/z. For each Orbitrap MS1 scan, $5 \times 10^5$ ions are accumulated over a maximum time of 500 ms. For each LTQ MS2 scan, $5 \times 10^3$ ions are accumulated over a maximum time of 250 ms. For each Orbitrap MS2 scan, $2 \times 10^5$ ions are accumulated over a maximum time of 1000 ms. The normalized collision energy for CID is set at 35%.

For ITA, MS2 of MSTIQ peptides is triggered by an inclusion list containing the m/z(s) of the index peptides with a 20 ppm window. Upon detection of an ion with an m/z that satisfies the inclusion criteria, MS2 scans are acquired on ions at the defined m/z away from that of the index peptide ions. For example, for index peptides with a Δm/z of +2 relative to the modified peptide of interest, the instrument is programmed to acquire ions with an m/z 4.5 units less than the m/z of the index peptide ion and within a two Dalton window. Index peptides are readily identified by accurate mass measurement, liquid chromatography (LC) retention time, and the presence of a minor peak −1/z units from the index peptide's monoisotopic m/z. This minor peak results from minor isotopic impurities in the isotopically heavy labeling reagents used to prepare the index peptides. Such unique index peptide features were observed (See, e.g., Example 7b and associated Figure).

Identification and Quantification of Peptides. Peptides may be identified from MS2 data using the SEQUEST database search algorithm (Eng, J. K., et al., *J. Am. Soc. Mass Spectrom.* (1994) 5:976-989). For quantification, the elution profile of index peptides is used to identify appropriate MS2 scans for quantification. Next, the ion intensities of all predicted peptide-specific fragment ions from the modified peptide of interest and the internal standard are extracted and the abundance ratios for each fragment ion pair are determined. A ratio is calculated by averaging the ratios from all fragment ions. Outliers are detected and removed. The final peptide ratio is calculated by averaging the abundance ratios determined from all MS2 scans acquired for the particular peptide.

To compute peptide abundance ratios, the intensities of each fragment ion pair i are quantified as $$x_i = \ln\left(\frac{\text{Intensity }(HL_i)}{\text{Intensity }(LH_i)}\right)$$

and outliers are detected with the "MAD-Median Rule" (see Wilcox, R. R. Introduction to Robust Estimation and Hypothesis Testing, 2d ed., Elsevier Academic Press, 2005, p. 101): $x_i$ is an outlier if $|x_i - M| > 3.321*m$; the choice of the constant 3.321 corresponds to a 5% chance of a rejecting a non-outlier from a normally-distributed sample), where $M = \text{median}\{x_i\}$ and $m = \text{MAD}(x_i) = 1.4826*\text{median}\{|x_i - M|\}$ denotes a robust estimate of the standard deviation based on the sample's Median Absolute Deviation (R mad( ) function). The final quantification for each identified peptide is mean $\{x_i\}$ after rejection of outliers. This "trimmed" mean estimate has known standard error $$s = \frac{s_W}{.95\sqrt{n}},$$

where $s_W$ is the sample Winsorized variance (see Wilcox, supra, p. 63). Finally, peptides are only considered "quantified" if at least two MSTIQ-labeled fragment ion pairs contribute to the trimmed mean. A MSTIQ ion is considered "observed" if its intensity $\geq$ SNR*BG; unless otherwise noted, SNR=2. Some potential MSTIQ fragment pairs may be excluded from quantification for one of three reasons: 1) all $b^{1+}$ and $y^{1+}$ fragment ion pairs were excluded; (2) any fragment ion pair containing a MSTIQ ion with a predicted m/z within ±1.5 Da of another predicted MSTIQ ion, or a neutral loss from a predicted ion (b-ions, loss of $NH_3$; y-ions, loss of $H_2O$), was excluded; and (3) any fragment ion pair for which the intensity of at least one MSTIQ ion was not "observed" was excluded. A fragment ion pair is generally deemed quantifiable if the intensity of one ion (HL- or LH-derived) was above background and the intensity of the sibling ion was non-zero.

For the iMSTIQ assay, automated scan selection for quantification is achieved using the same constraints described for MSTIQ. In addition, the index peptide ion elution profiles are used to assist in scan selection. Ion intensities for the predicted monoisotopic index peptide ion peak (±20 ppm), as well as intensities for peaks at +1/z and −1/z, are extracted. Elution of an index peptide ion is distinguished from other ions based on two criteria. First, a scan is considered to contain an index peptide ion if intensities of 0.05-0.35x (−1/z peak) and 0.5-1.5x (+1/z peak) the predicted index peptide ion's monoisotopic peak intensity are present. Second, only MS2 scans triggered from MS1 scans with an index ion intensity of $\geq$10% of the peak index ion elution intensity are considered. MS2 scans without this evidence of an intense, co-eluting index ion are rejected. Other than these differences, scan selection and quantification are the same as for MSTIQ. Scans were selected automatically for the iMSTIQ study in Example 7 and entirely manually for the macrophage study in Example 8.

EXAMPLES

The following examples are offered to illustrate but not to limit the invention.

Example 1

Preparation of Boc-L-Alanine N-Succinimidyl Ester (Boc-Ala-OSu)

To prepare the isotopically light MSTIQ reagent, Boc-Ala-OSu, a mixture of Boc-alanine (1 equiv., NovaBiochem), N-hydroxysuccinimide (1 equiv., Sigma, St. Louis, Mo.), and N,N'-diisopropylcarbodiimide (DIC, 1 equiv., Sigma) in anhydrous N,N-dimethylformamide (DMF, 0.3 M, Fisher) was incubated overnight at room temperature. After overnight incubation, the supernatant containing Boc-Ala-OSu was isolated and was used directly. Alternatively, Boc-Ala-OSu was purchased from Sigma-Aldrich.

An isotopically heavy MSTIQ reagent, Boc-($^{13}C_3^{15}N$)-Ala-OSu was prepared from isotopically labeled Boc-($^{13}C_3^{15}N$)-Ala (Cambridge Isotope Laboratories, Andover, Mass.) using the method described above.

Example 2

Labeling of Peptides of Interest with an MSTIQ N-Terminal Labeling Reagent

Tryptic peptides derived from macrophage lysates were prepared according to standard methods.

To a suspension of the tryptic peptides (30 µg) in 0.5 M Hepes buffer pH 8 (20 µL) was added Boc-($^{13}C_3^{15}N$)-Ala-OSu (30 µL, 0.15 M in DMF) dropwise with frequent mixing. After incubating for 35 minutes, the mixture was treated with conc. HCl (45 µL) by dropwise addition with frequent mixing. After 30 min at room temperature, the mixture was cooled on ice and treated with 1 M Tris base pH 8.3 (50 µL) to quench any unreacted MSTIQ reagent. The acid was partially neutralized by the repeated addition of 1 M NaOH (5×156 µL), with vortexing, until the pH reached ~3. The sample was diluted with 0.5% acetic acid to reduce the DMF concentration to below 2-3%. Labeled peptides were then purified by $C_{18}$ chromatography.

Example 3

Preparation of MSTIQ Standard Peptides

Variation 1. A peptide comprising the sequence of the peptide of interest with an isotopically light C-terminal lysine tag is prepared by standard peptide chemistry methods or purchased commercially (Peptide 2.0 Inc., Chantilly, Va.; Genscript Co., Scotch Plains, N.J.). For the experiments described herein, light peptides were purchased at a crude purity level. The peptide is then labeled by reaction with the isotopically heavy version of the MSTIQ reagent, Boc-($^{13}C_3^{15}N$)-Ala-OSu, and purified as described in Example 2.

Variation 2. MSTIQ standard peptides with N-terminal alanine residues and isotopically heavy C-terminal $^{13}C_6^{15}N$-lysine residues were purchased commercially (Sigma; >95% purity; isotopic content: 98% $^{13}C$, 98% $^{15}N$).

Example 4

Preparation of ITA Index Peptides

Exemplary ITA index peptides derived from the sequence of the peptide of interest and modified with isotopically heavy alanine residues at the N-termini and isotopically heavy lysine residues at the C-termini were prepared as follows: Peptides lacking N-terminal alanine residues but incorporating C-terminal isotopically heavy lysine residues ($^{13}C_6^{15}N$) were purchased commercially (Sigma; >95% purity; isotopic content: 98% $^{13}C$, 98% $^{15}N$). The peptides were labeled at the N-termini by reaction with the isotopically heavy MSTIQ reagent, Boc-($^{13}C_3^{15}N$)-Ala-OSu, as described in Example 2.

Example 5

Evaluation of Quantitation Provided by MSTIQ Method

MSTIQ's quantitation was evaluated by measuring the relative levels of proteins in mouse macrophage lysates and comparing these measurements to the known levels.

Example 5a

RAW264.7 cells (ATCC, Manassas, Va.) were grown at 37° C. with 5% $CO_2$ on SILAC-specific RPMI-1640 media (Caisson Laboratories, North Logan, Utah), supplemented with 10% dialyzed fetal bovine serum (Invitrogen, Carlsbad, Calif.), 1% Pen/Strep (Invitrogen), 2 mM L-Glutamine (Invitrogen), and with either light Lys and Arg amino acids or heavy Lys ($^{13}C_6^{15}N_2$) and Arg ($^{15}N_4$) amino acids. The "heavy" and "light" batches were processed separately as follows. After five passages, cells were activated by 100 ng/ml LPS (Sigma) for 4 h prior to harvest. The collected cells were lysed in 25 mM HEPES, 150 mM NaCl, 5 mM $MgCl_2$, 1% TritonX-100, 0.05% SDS, 1 mM EDTA, and protease inhibitor cocktail (Roche) on ice for 30 min. Following centrifugation at 18,200 g for 10 min at 4° C., the supernatant cell lysate was collected and stored at −80° C. until further processed. Proteins in the cell lysate were denatured with 1 mg/ml (w/v) RapiGest (Waters, Milford, Mass.) and 0.1% SDS (Mediatech, Herndon, Va.) at 95° C. for 10 min, reduced with 5 mM TCEP [tris(2-carboxyethyl)phosphine, Thermo Scientific, Waltham, Mass.] at 60° C. for 1 h, and alkylated with 12.5 mM iodoacetamide (Sigma) at 37° C. in the dark for 30 min. The sample was diluted 10-fold with 100 mM TEAB (triethylammonium bicarbonate, Thermo Scientific) prior to digestion with sequencing grade modified trypsin (Promega) at 1:50 (w/w) enzyme to substrate ratio overnight at 37° C. The resulting heavy or light peptides (labeled via SILAC at C-termini) were then labeled with light (Δ0) or heavy (Δ4) mTRAQ® reagents (Applied Biosystems) respectively to generate isobaric peptides.

The two isobaric peptide samples were mixed at ratios of 1:30, 1:10, 1:3, 1:1, 3:1, 10:1, and 30:1. The peptide mixtures were purified on MCX µElution plates (Waters) prior to LC-MS/MS analysis. The mixtures were analyzed using intensity-based, data dependent acquisition (DDA) followed by an X!Tandem search to identify peptides. The DDA mode was applied to conduct 4 MS2 scans on the most abundant precursor ions detected in each MS1 scan. MS1 signals exceeding 500 counts were chosen for CID. An isolation window of 1.0 m/z was used and the selected precursor ions were dynamically excluded for 60 s.

The seven datasets were each searched twice against the Mouse International Protein Index (IPI) database (v.3.56) augmented with the reversed sequences as decoys, using X!Tandem as described above with the following parameter changes: a fixed modification of +57.021464 on Cys was used; one search was conducted with fixed modifications on N-termini (+144.1021) and Lys (+144.1021) to account for HL peptide modifications; the other search was conducted with fixed modifications on N-termini (+140.095), Lys (+148.1092), and Arg (+3.98814) to account for LH peptide modifications. Peptide identification was achieved by processing the search results with the TPP.

Confidently identified peptides (fully-tryptic, 2+ and 3+ ions with no missed cleavages, PeptideProphet probability$\geq$0.9) in at least one of the seven titers were evaluated for quantification in all seven datasets using ISBquant software (available from Institute for Systems Biology on request). In addition to these positively identified scans, ISBquant considers other scans for quantification if the theoretical and observed m/z's are within 0.5 units of each other and at least 7 HL or 7 LH fragment ions in the scan are observed above background level (BG, defined as the $25^{th}$ percentile of all non-zero intensities in the scan). This enabled some peptides to be quantified in titers in which they did not pass the PeptideProphet threshold of 0.9. Scan selection was further restricted by identifying the highest quality scan, and only scans with a retention time $\leq \pm 1$ min from the highest quality scan were used for quantification. For this purpose, scan quality was judged by the number of observed HL or LH MSTIQ ions (whichever was greater); ties were broken by the median observed MSTIQ ion intensity in each scan. In addition to automatic scan selection (applied in FIG. 3), ISBquant allows for manual scan selection by the user.

Figure 3A:
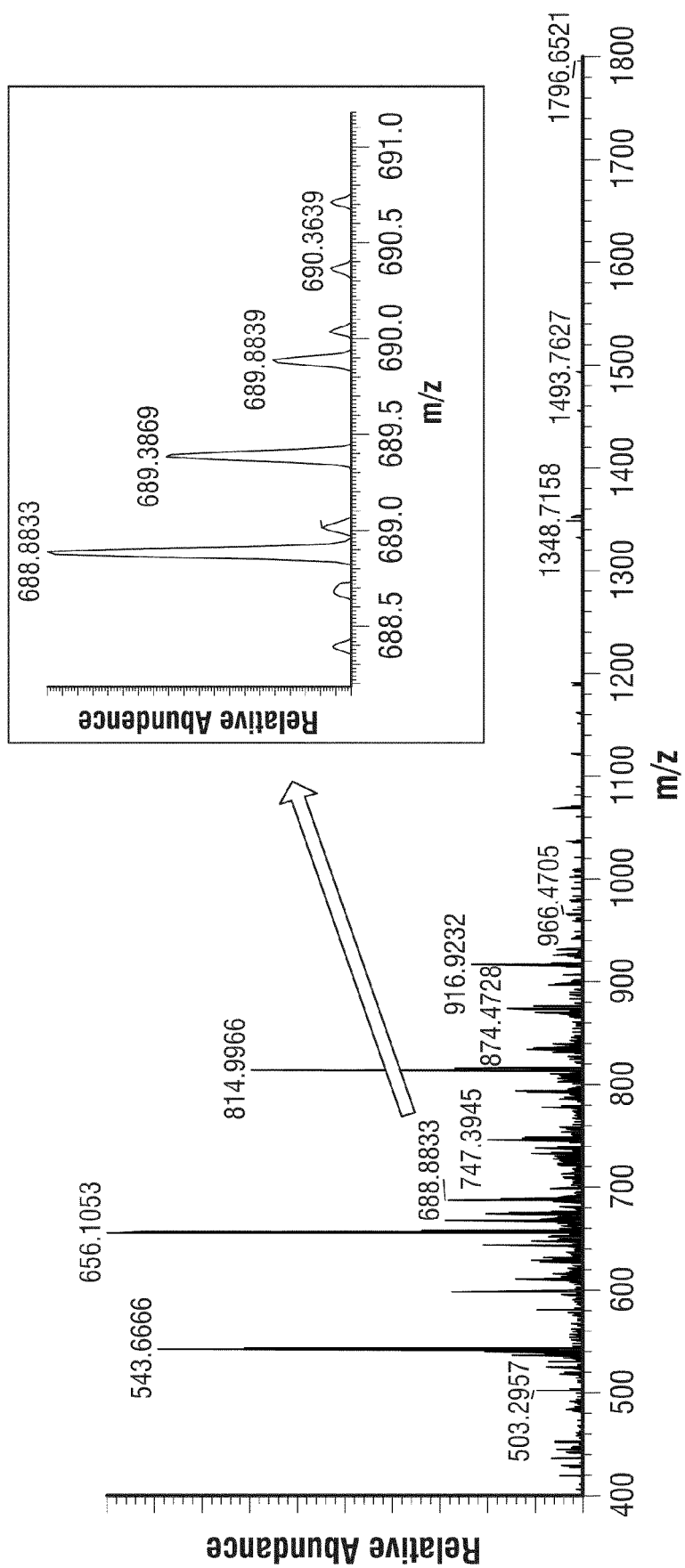
FIGS. 3A-C. Results of the MSTIQ peptide quantification experiment described in Example 5. (A) Full scan MS1 spectrum (400-1800 m/z) at an LC retention time of 59.48 min. Inset: isotopic distribution of the representative peptide "LWTLVSEQTR" ($[M+2H]^{2+}$, m/z 688.88). (B) Full scan MS2 spectrum (175-1390 m/z) of the precursor peptide from (A). Multiple b- and y-ion pairs are shown. Insets: Expanded views of representative pairs of 1+ fragment ions, appearing 4 Da apart; as expected, relative peak intensities for each pair are approximately 1:1. (C) Expected vs. measured abundance ratio (ln(HL/LH)) for all seven titers. Medians (M, dots) and range (M±2 s; bars) are shown for each titer. Histograms show values in the range; counts above, below, or beside each histogram represent peptides with ratios higher, lower, or within the range, respectively.
Figure 3B:
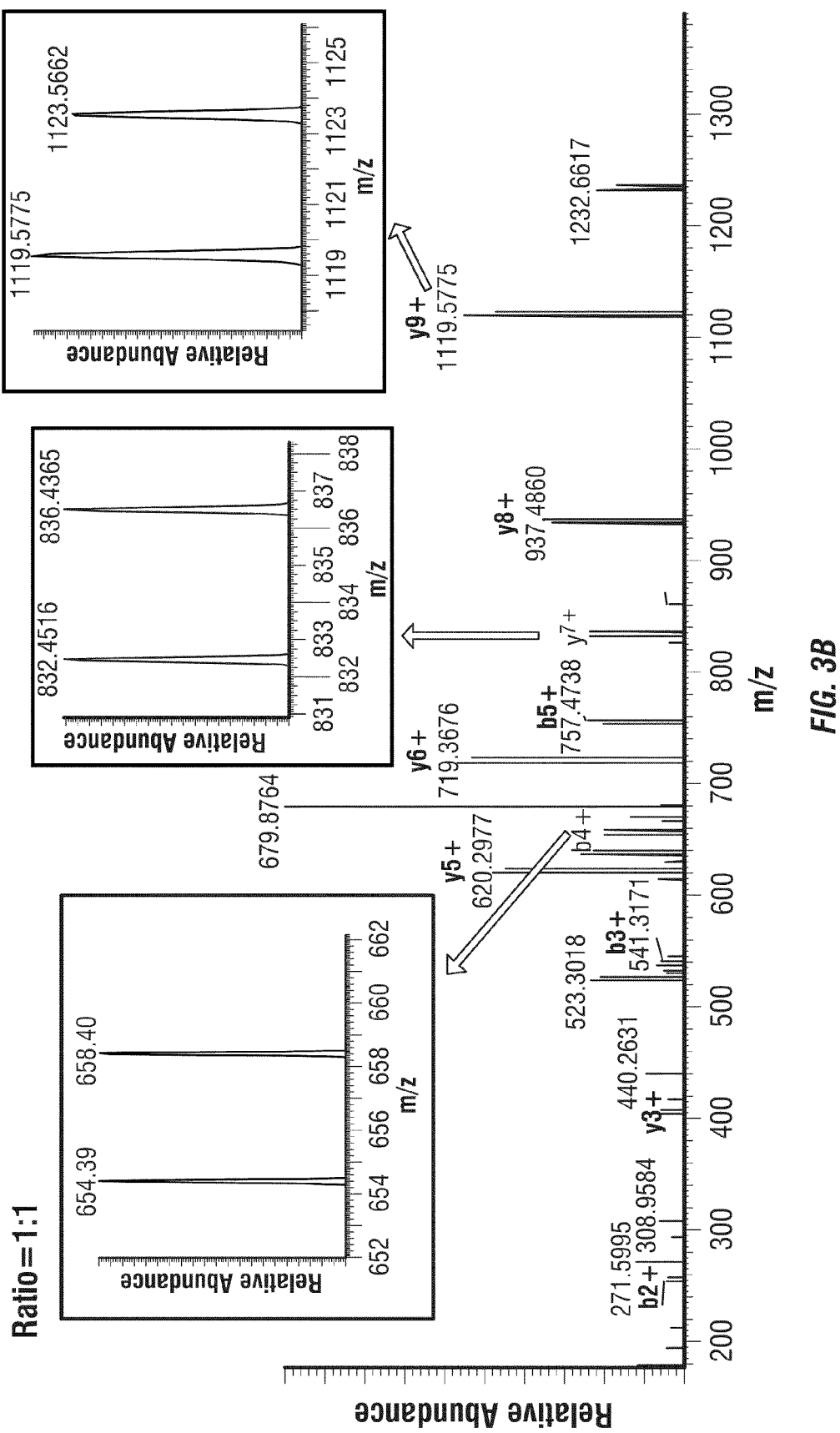
Figure 3C:
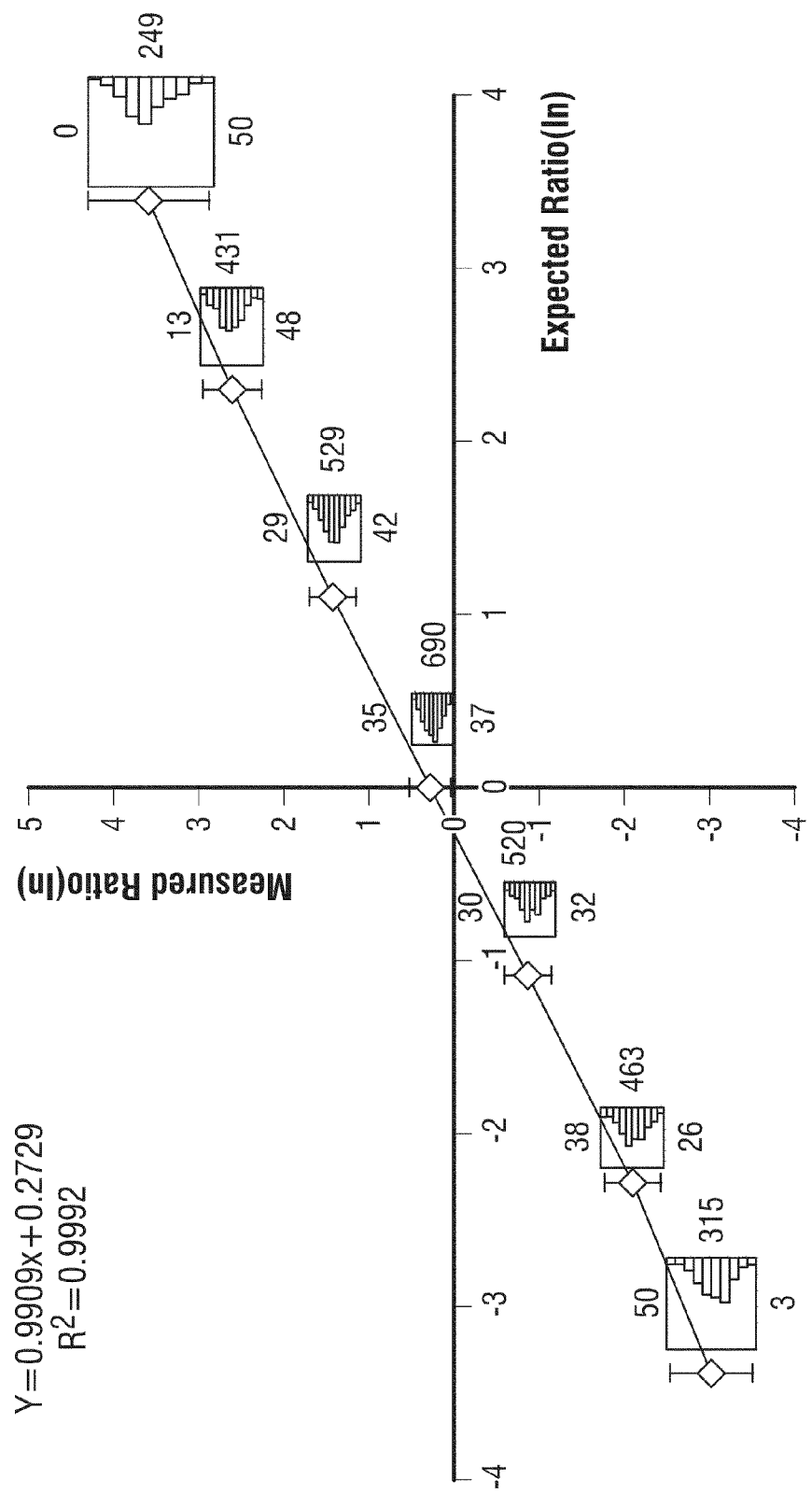

The results for this experiment are shown in FIG. 3. FIG. 3(a) shows the full MS1 scan, and FIG. 3(b) shows the MS2 spectra for one representative peptide, "LWTLVSEQTR", which was identified in the 1:1 mixture. The monoisotopic peak ($[M+2H]^{2+}$) of the isobaric, MSTIQ-labeled peptide pair appears at 688.88 m/z in the MS1 spectrum. Fragmentation of this precursor ion generated a series of b- and y-ions appearing as isotopic pairs in the MS2 spectrum. The spectra for three representative fragment ion pairs ($b4^+$, $y7^+$, and $y9^+$) are shown in expanded views (insets). Two peaks separated by four m/z units were observed for each fragment ion pair and their relative peak intensities were approximately 1:1, as expected.

The relative abundances of the HL and the LH peptides in each titration experiment were evaluated by examining a total of 1080 peptides that were positively identified (PeptideProphet p$\geq$0.9, FDR$\leq$1.5%) in at least one titration. ISBquant (Isobaric quantification) software (available from Institute for Systems Biology) computes an abundance ratio (HL/LH) for each peptide using the intensities of the quantifiable peptide-specific fragment ion pairs. The ratios for all peptides quantified in each titer are summarized in FIG. 3(c). Excellent linearity ($R^2$=0.9992) between the MSTIQ-measured and expected ratios was observed over the full range of relative abundances (1:30 to 30:1). The accuracy of the method is indicated by the histograms of individual peptide quantifications within two standard deviations of the calculated median; 50% of the quantifications have a relative error$\leq$13%. See FIG. 3(c).

These results demonstrate that MSTIQ is an effective method for accurate quantification of peptides in complex mixtures over a wide dynamic range.

Example 6

Improved Sensitivity of ITA Method

The sensitivity of the ITA method for peptide detection was compared to the sensitivity of an inclusion list method. The methods were evaluated as to their ability to select predetermined peptides for MS2 analysis and to identify them.

Yeast strain (BY4741, Mata, his3$\Delta$1, leu2$\Delta$0, met15$\Delta$0, ura3$\Delta$0) grown in YPD media to log phase was harvested and bead-beaten in lysis buffer (50 mM HEPES, pH8.0, 1% SDS, 150 mM NaCl) with protease inhibitor cocktail (Roche, Mannheim, Germany). The protein extract was then acetone precipitated and dissolved in 10 mM Tris-HCl, pH 8.0 containing 1 M urea. The protein mixture was then treated with 5 mM DTT, alkylated with 15 mM iodoacetamide, and trypsin digested overnight. The trypsin digested peptides were purified by $C_{18}$ spin column (The Nest Group, Southboro, Mass.) prior to use for mass spectrometry analyses.

Sixty-five (65) lysine-terminal AQUA® peptides corresponding to mouse or human proteins were alkylated with 6 mM methyl methanethiosulfonate (MMTS) and then labeled with heavy ($\Delta$4) or light ($\Delta$0) mTRAQ® reagents (Applied Biosystems) following the manufacturer's protocol, to generate the heavy and light isobaric peptide pairs with 8 Da mass differences. Another 21 lysine-terminal AQUA® peptides (used as heavy forms) were also included along with their synthetic light peptide variants. The heavy variants of the peptides (index peptides) were spiked into 1 µg yeast peptide mixture at 500 fmol each, and the light variants ("modified target peptides," acting as modified peptides of interest) were spiked in at a low fmol level at a different concentration for each of four experiments (0.75, 3.75, 7.5, or 15 fmol).

The samples were analyzed separately by either ITA or an inclusion list method using an LTQ-Orbitrap instrument. Five MS2 scans were acquired following each MS1 scan. The threshold for MS2 analysis was set at 2,000 counts, dynamic exclusion was set at 1 event for 10 seconds, and a CID isolation window of 1.1 m/z was used. Charge state screening was applied with only +2 or +3 charged ions being analyzed per MS run. In the inclusion list method, the m/z of the modified target peptide ion was put on the parent mass inclusion list and detection of an ion at that m/z triggered fragmentation of ions at that m/z. For ITA, the m/z value of the index peptide ion was put on the parent mass list, and detection of an ion at the index ion m/z also triggered fragmentation of ions at the modified target peptide m/z (e.g. $\Delta$m/z=−4 m/z units for +2 ions). For the +2 charged ions, a mass of "−4.0000" was set in the "Add/Subtract" feature; for the +3 charged ions, a mass of "−2.6667" was applied. Data from both analyses were searched with X!Tandem against a yeast database also containing the targeted peptide sequences. Correctly identified peptides from each analysis are shown in Supplementary Table 1 (FDR<5%).

The acquired MS2 spectra were searched against a yeast database (yeast.nci.20080206) supplemented with the sequences of the targeted peptides using X!Tandem. The following search parameters were applied: full tryptic cleavage specificity; mass tolerance of ±20 ppm for precursor ions and 0.4 Da for fragment ions; no missed cleavage allowed; fixed modification on Cys (+45.9877 Da) and variable modifications on Met (+15.9949), Lys (+148.1092) and N-termini (+140.095). Peptide identification was achieved by processing the search results with the Trans-Proteomic Pipeline (TPP, located on the World Wide Web at tools.proteomecenter.org/wiki/index.php?title=Software:TPP).

Figure 4:
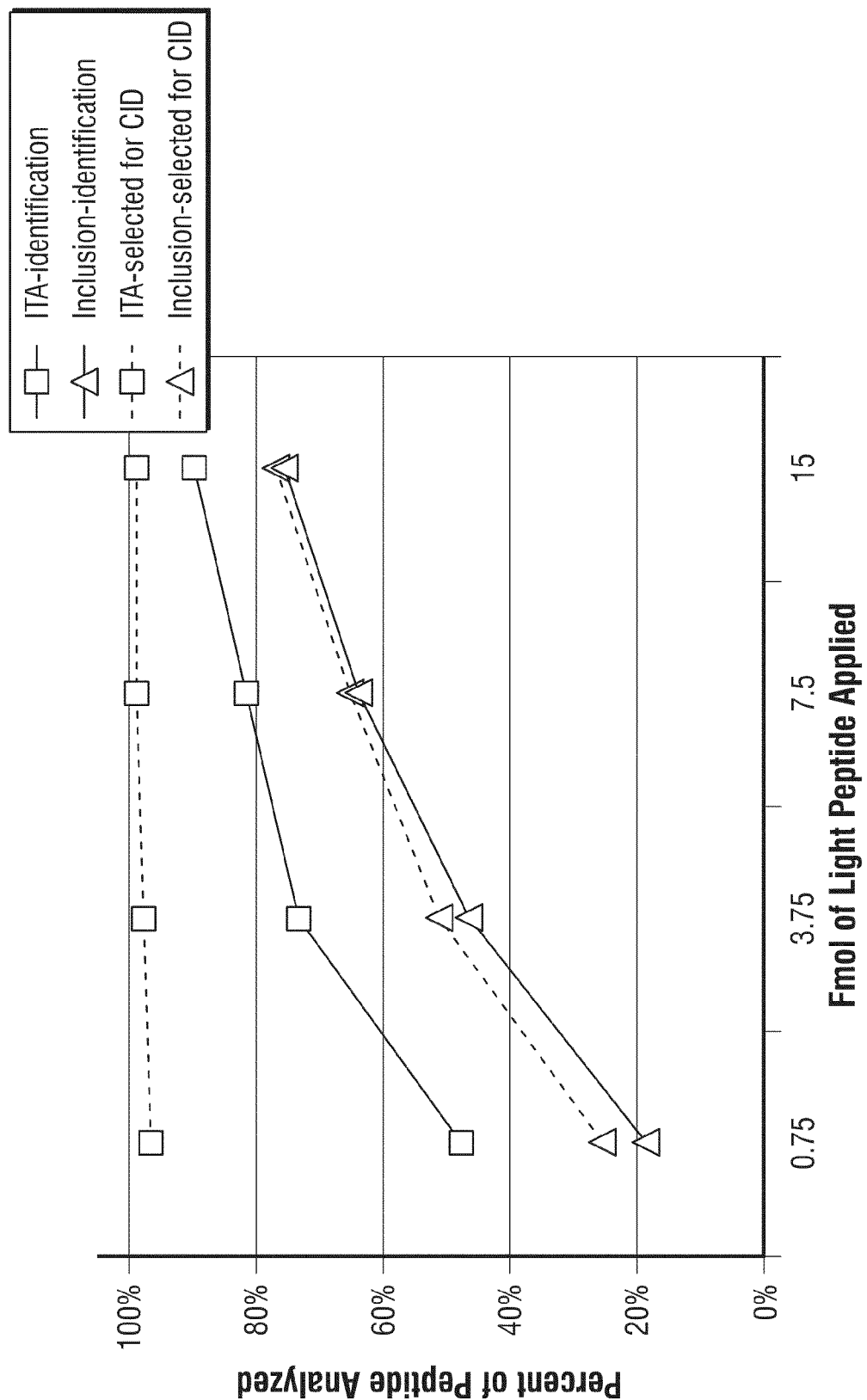
FIG. 4. Results from the ITA detection experiment described in Example 6. Eighty-six (86) peptides were spiked into a tryptic digest derived from a whole cell yeast protein extract at the indicated amounts and targeted for identification using either ITA (squares) or an inclusion list method (triangles). The percentage of peptides selected for CID (dashed lines) or identified (solid lines) by each method are plotted as a function of the quantity of peptides that were spiked into the sample.

As summarized in FIG. 4, ITA outperformed the inclusion list method in all four titration experiments in terms of correct selection of target peptides for MS2 analysis, as well as their positive identification. The performance of the ITA method was particularly enhanced when the lowest amounts of target peptides were analyzed. In the analysis of samples containing 0.75 fmol of target peptides, ITA correctly triggered MS2 analysis on 97% of the targeted peptides, while the inclusion list method correctly triggered MS2 analysis on only 26% of the peptides. This improvement in triggering was reflected in improved rates of peptide identification: at 0.75 fmol of target peptides, 48% of the peptides were identified via ITA whereas only 19% of the peptides were identified via the inclusion list method. Importantly, ITA showed consistently high rates of correct MS2 triggering in all four experiments (96.51%, 97.67%, 98.84%, and 98.84% respectively). These results demonstrate that ITA ensures reliable triggering of MS2 events on target peptides, and indicate that ITA significantly improves rates of peptide identification.

Example 7

Determination of the Limit of Quantitation for the iMSTIQ Method

The limit of quantification (LOQ) of iMSTIQ was assessed by spiking MSTIQ-labeled peptides into a sample of glycopeptides isolated from human serum.

Human serum (10 mg, 137 µL; Bioclamation, Hicksville, N.Y.) was used for the hydrazide-based solid-phase capture of the N-glycosylated peptides as previously described (Tian, Y., Zhou, Y., Elliott, S., Aebersold, R. & Zhang, H. Solid-phase extraction of N-linked glycopeptides. Nat Protoc 2, 334-339 (2007)). The resulting N-glycosylated peptide mixtures were dissolved in 137 µl 0.1% formic acid.

Example 7a

For the peptide of interest, SQVQASYTFK, the isobaric MSTIQ peptide pair (LH, HL) and the index peptide were prepared as indicated in the following scheme.

Scheme:

MSTIQ Peptide Preparation:

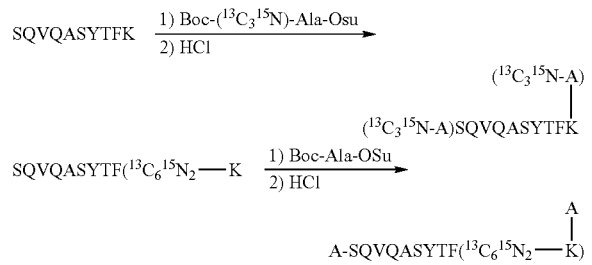

Index Peptide Preparation:

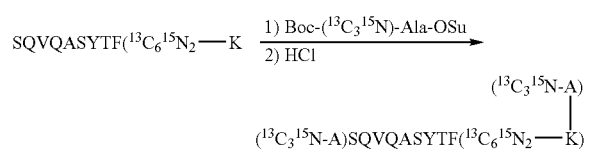

Figure 5:
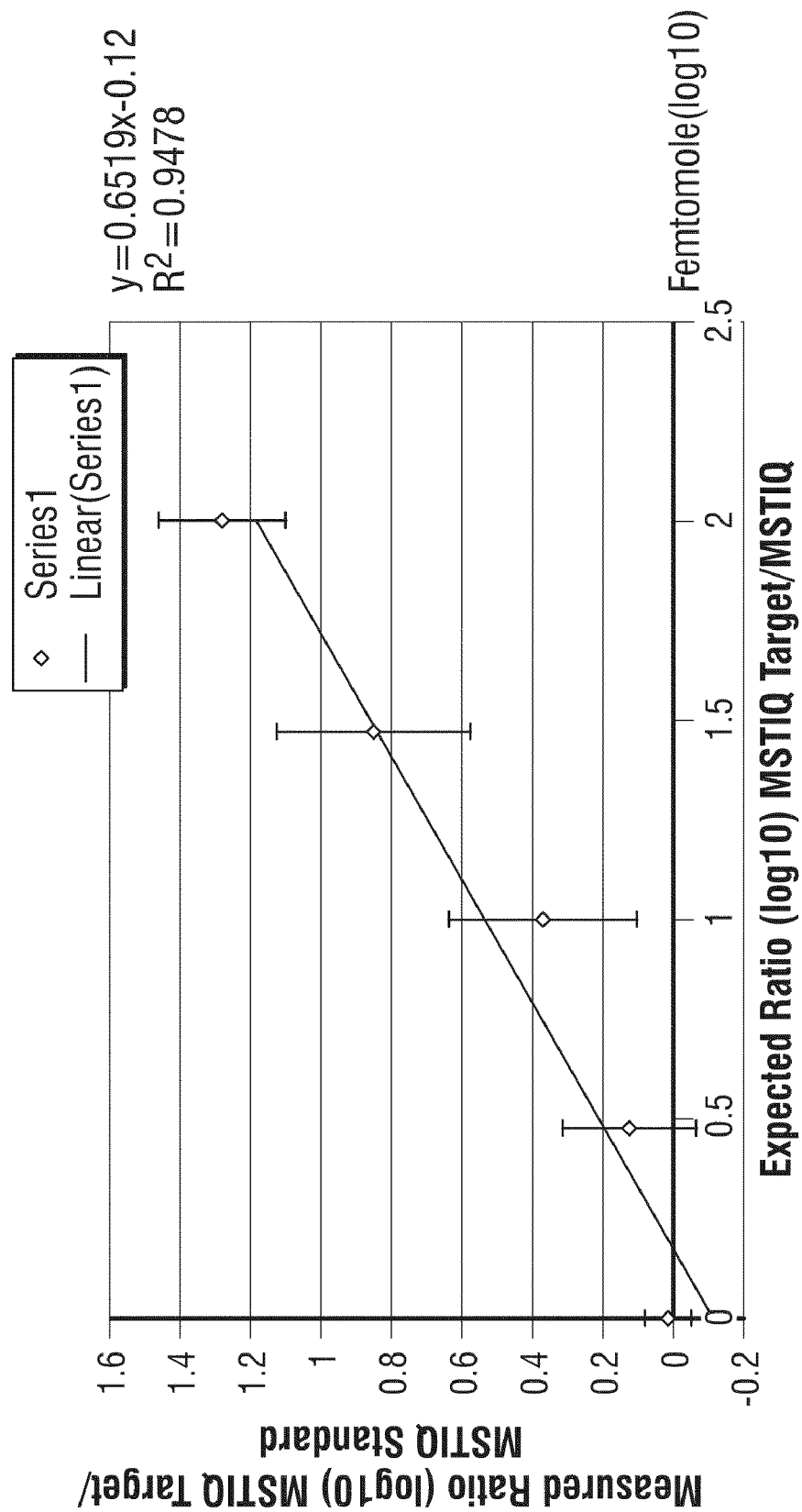

Samples were prepared with from 1 to 100 femtomole of the modified peptide of interest, labeled at the N-terminus with the heavy version of the iMSTIQ reagent, in 1 µg of the glycopeptides mixture. To each sample, 1 femtomole of the internal standard, labeled with the light version of the iMSTIQ reagent, was added. The index peptide (500 fmol) was added to trigger MS2 analysis for the MSTIQ isobaric peptide pair. As shown in the FIG. 5, the target peptide level was successfully quantified from a complex background at amounts ranging from 1 to 100 femtomole by comparison to the ion intensities generated by fragment ions from the internal standard. A linear regression was obtained within this range for accurate quantification.

Example 7b

To evaluate the performance of iMSTIQ in complex samples such as blood, a pair of MSTIQ peptides ["FAISYQEK", HL (95% purity) and LH (crude)] was prepared (analogously to Scheme 1) and spiked at ~3 fmol each into an N-glycopeptide mixture (~1 µg) isolated from 1 µL human plasma. The HH peptide (100 fmol) was spiked into the same sample to serve as the index peptide. Three MS2 analyses were carried out following each MS1 scan in which signals exceeding 100 counts triggered CID without dynamic exclusion, and a CID isolation window of 3.0 m/z was used. Charge state screening was used to limit ion selection to +2 charge states only. A "parent mass list" containing the m/z values of the index peptides was used to trigger CID on ions with m/z values equal to m/z (index peptide)–3.6000 Da using the "Add/Subtract" feature.

Figure 6A:
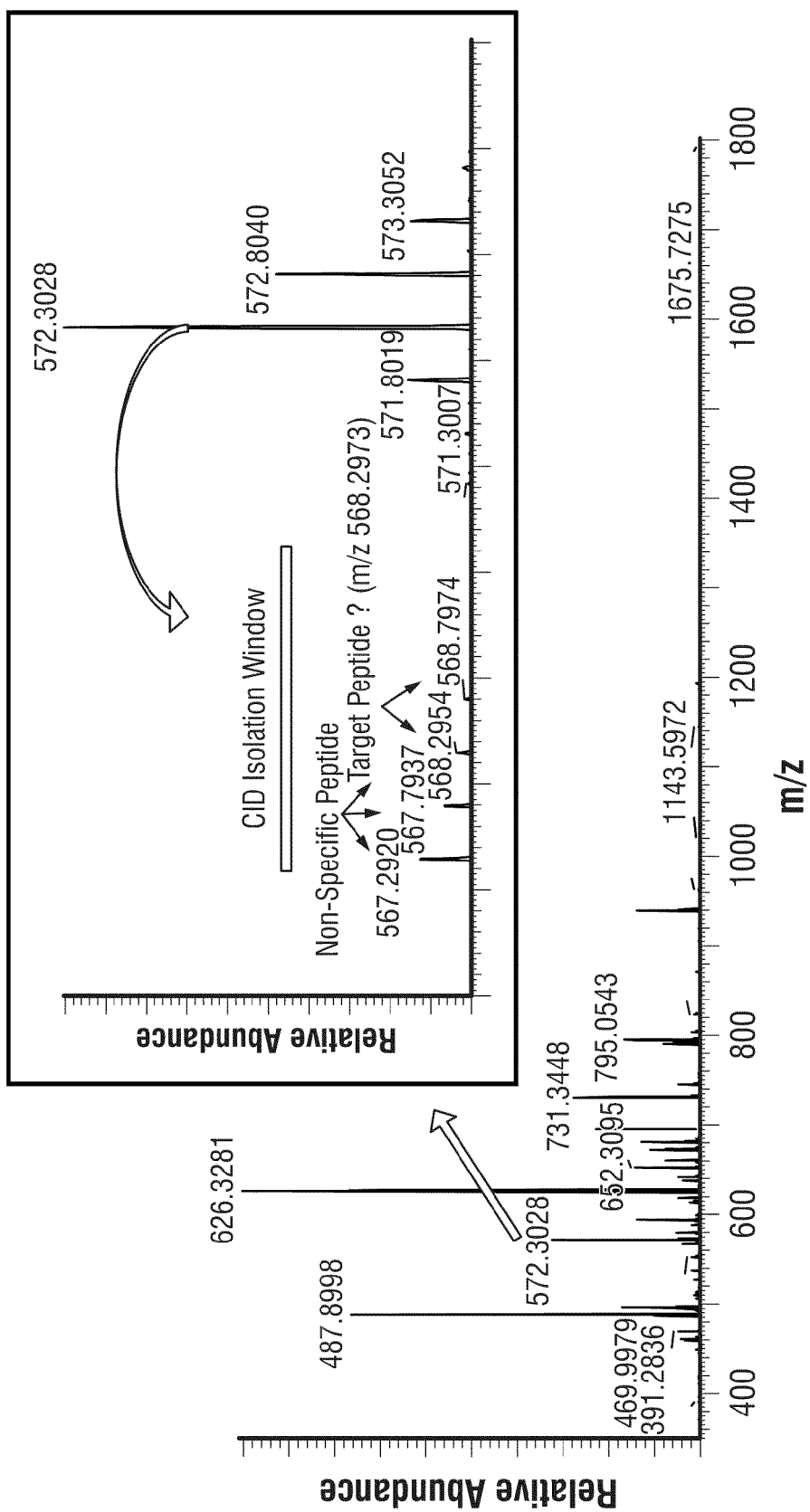
FIGS. 6A-C. Results of Examples 7b and 7c. Example 7b: (A) Full MS1 spectrum (350-1,800 m/z) at an LC retention time of 41.41 min. Inset: Expanded view (566-575 m/z) showing the index peptide parent ion for a representative peptide "FAISYQEK" ($[M+2H]^{2+}$, 572.3028 m/z). Targeted peptides ($[M+2H]^{2+}$, 568.2973 m/z) and a co-eluting non-specific peptide ($[M+2H]^{2+}$, 567.2920 m/z) are within the CID isolation window (567.2-570.2 m/z, bar). (B) Full MS2 spectrum (145-1150 m/z) triggered by the index peptide in (A). Positively identified peptide-specific fragment ion pairs are marked. The targeted MSTIQ fragment ion pairs have lower intensities than the fragment ions corresponding to the non-specific peptide (singlet fragment ion pattern). Insets: Expanded views of MS2 spectra for representative fragment ion pairs (4 Da apart) each with a relative abundance close to 1:1. Example 7c: (C) Plots of log(LH/HL) vs. the known amount of each internal standard (LH) peptide (log scale). A consistent linear regression is observed for $1 \leq LH \leq 30$ fmol.
Figure 6B:
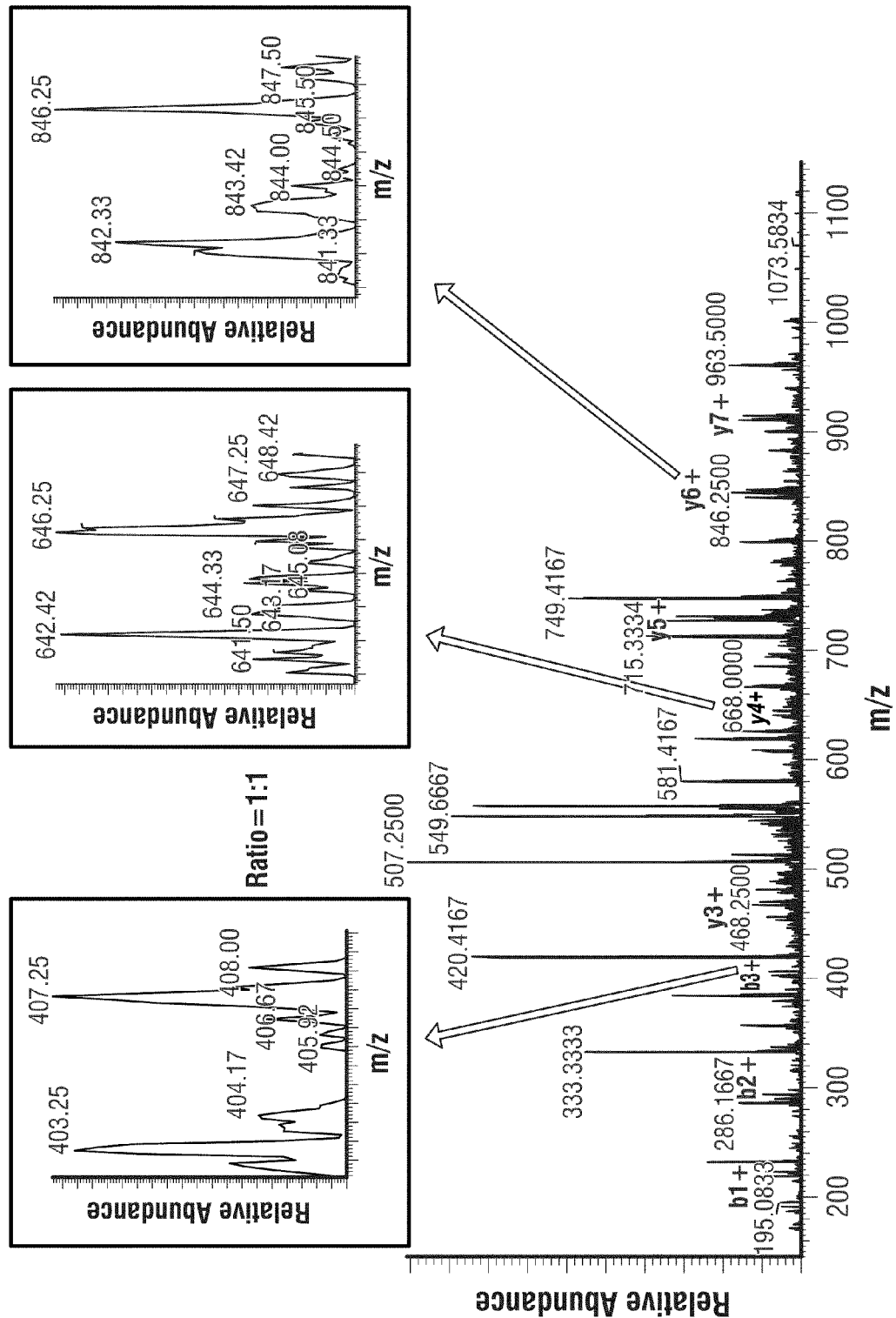

FIG. 6(a) shows a representative full MS1 scan at the time when the targeted MSTIQ peptide pair and the index peptide eluted; an expanded view of 566 to 575 m/z is shown in the inset. Detection of the peak at 572.3028 m/z (corresponding to the index peptide ion) triggered CID on ions within a window of 567.2-570.2 m/z according to the preset ITA program. As shown in the inset, the targeted peptide ion (568.2973 m/z) is either not detectable or overlaps with an isotopic peak (568.2954 m/z) of a non-specific ion (567.2920 m/z). If an inclusion list method had been used under these circumstances, it is likely a CID for the targeted ion would not have been initiated due to the low abundance of the target ion and/or the inability of the instrument to distinguish the targeted ion from the co-eluting ion. Nonetheless, ITA correctly triggered CID as shown by the presence of a series of fragment ion pairs specific to the targeted peptide in the MS2 spectrum (FIG. 6(b)). As a result, the targeted peptide was positively identified and quantified. Consistent with the observed complexity of the MS1 spectrum, in the MS2 spectrum the intensities of the MSTIQ fragment ion pairs (identified doublets; insets) are much lower than the intensities of the fragment ions derived from the co-eluting ion (observed as singlets). The iMSTIQ method permits identification and quantification of target peptides in complex mixtures even if they co-elute with other ions. If a reporter ion strategy such as iTRAQ or TMT was used, it would not be possible to distinguish the signals from the target peptide and co-eluting peptides, and this could compromise the accuracy of quantification. With iMSTIQ, the abundance ratio was determined based on multiple pairs of fragment ion (FIG. 6(b)).

Example 7c

To evaluate the range of quantification for iMSTIQ in the complex, human glycoplasma mixture, quantification of the "FAISYQEK" peptide and seven other synthetic peptides was examined at various concentrations. Eight (8) tryptic peptides carrying either the heavy ($^{13}C_6^{15}N_2$) or light C-terminal Lys tags were chemically synthesized via the Sigma AQUA® platform (95% purity). The heavy peptides were then labeled with either the heavy version of the MSTIQ reagent, Boc-($^{13}C_3^{15}N$)-Ala-OSu, to generate the index peptides (HH), or the light version of the MSTIQ reagent to generate the LH peptides. Similarly, the light synthetic peptides were labeled with the heavy MSTIQ reagent to generate the HL peptides. The labeled peptides were purified on MCX μElution plates.

Figure 6C:
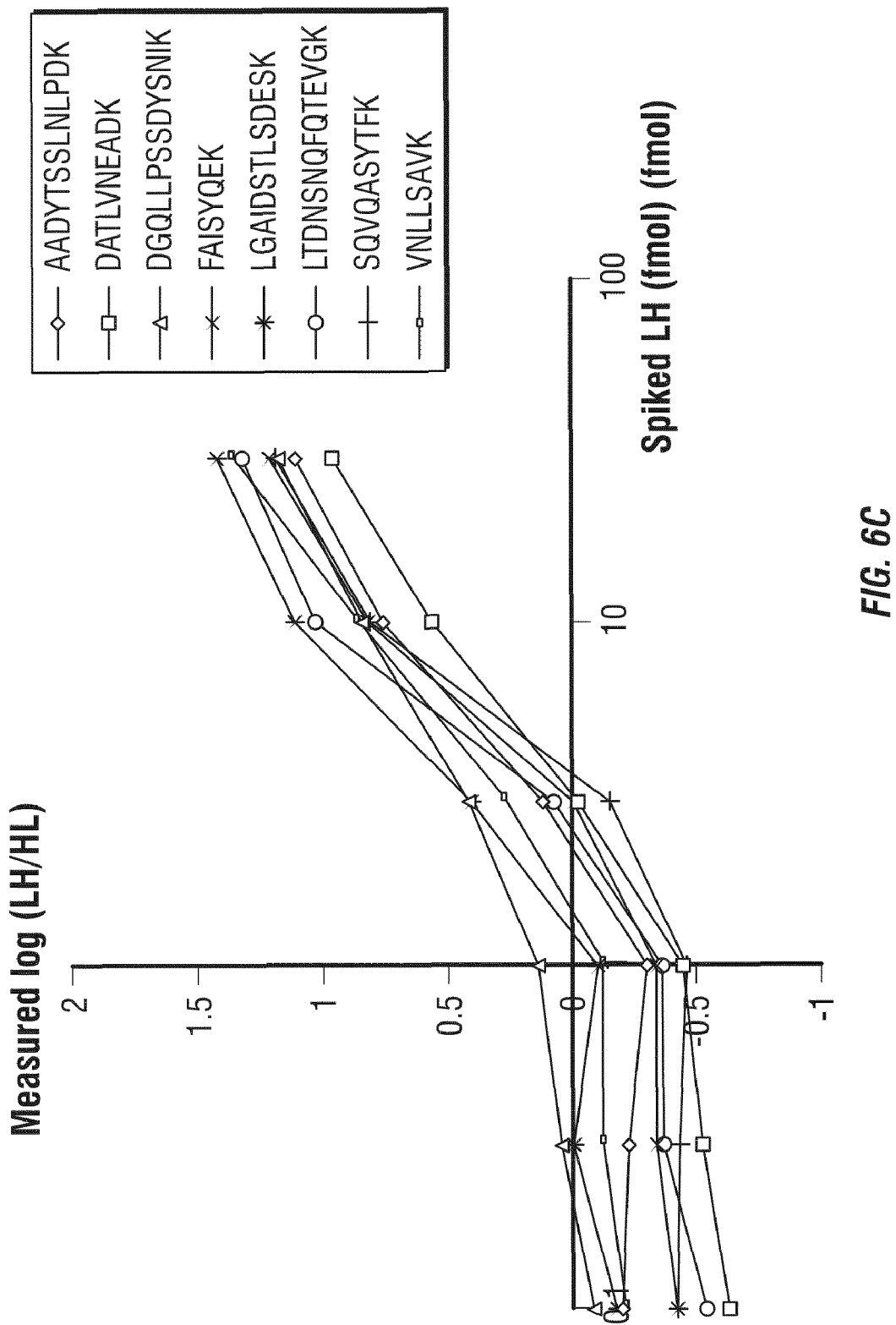
Figure 7A:
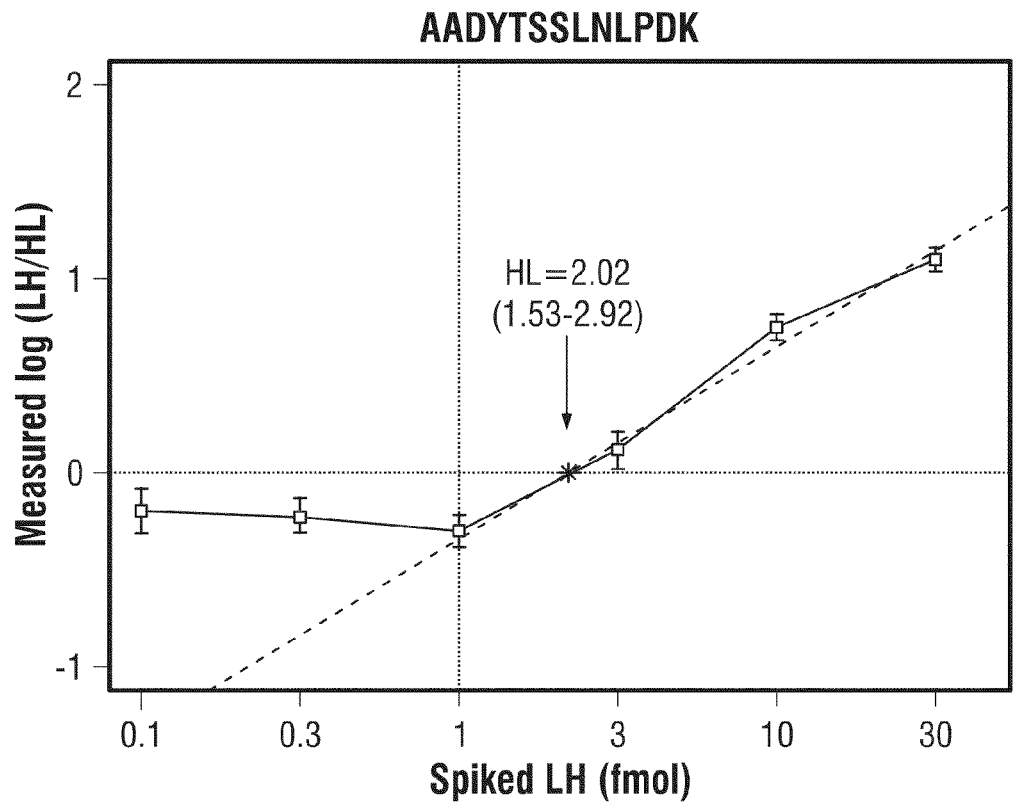
FIGS. 7A-H. Results from Example 7c. Plots of log(LH/HL) vs. the known amount of LH internal standard peptide (log scale) for each of the eight examined peptides. The amount (h) of the crude HL peptide was estimated by fitting $\log_{10}(LH/HL) = \log_{10}(LH) - h$ (dotted line) to the data with $LH \geq 3$ fmol (filled circles; h is shown as the mean estimate, with a range of 2 standard deviations transformed to the linear scale, $h = 10^\mu$, ($10^{\mu - 2\sigma} \leq h \leq 10^{\mu + 2\sigma}$)). Note: For peptide DGQLLPSSDYSNIK, h was not within the linear range and therefore may not be accurate (marked with asterisk).
Figure 7B:
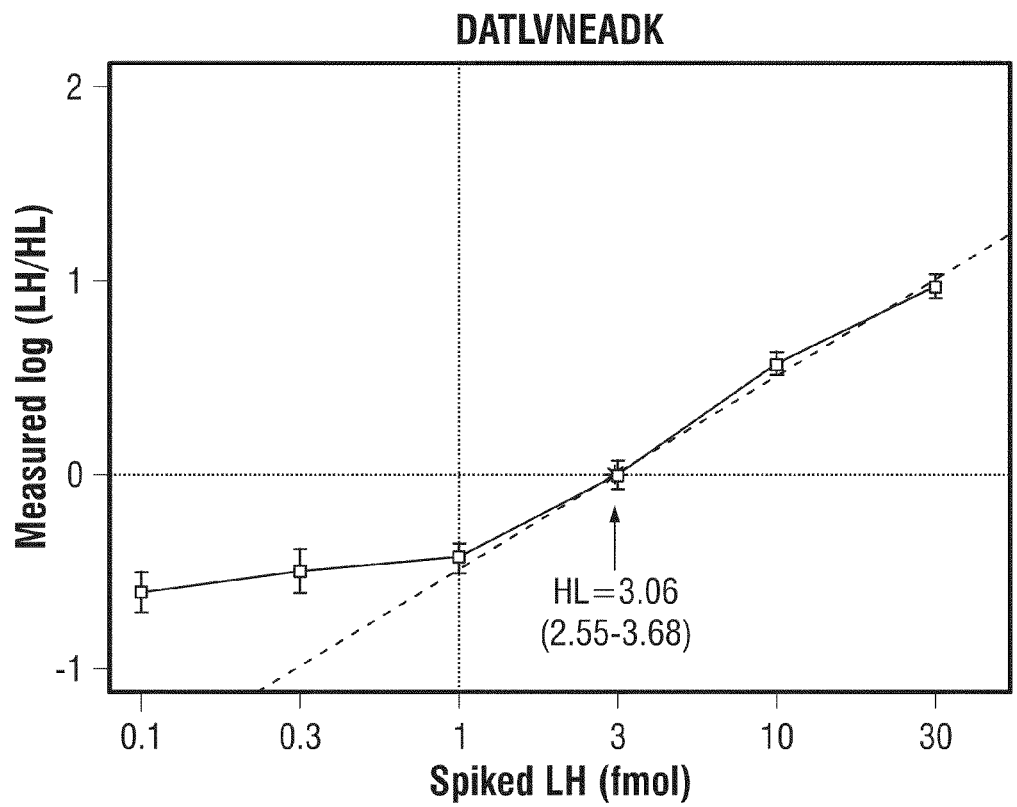
Figure 7C:
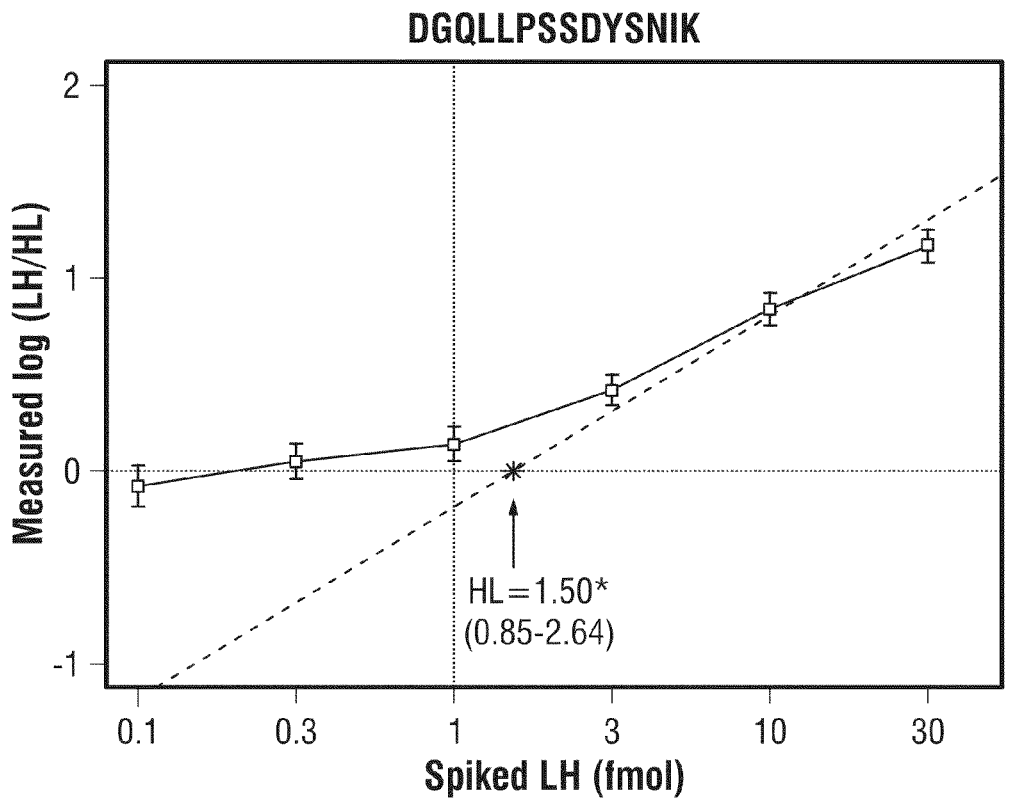
Figure 7D:
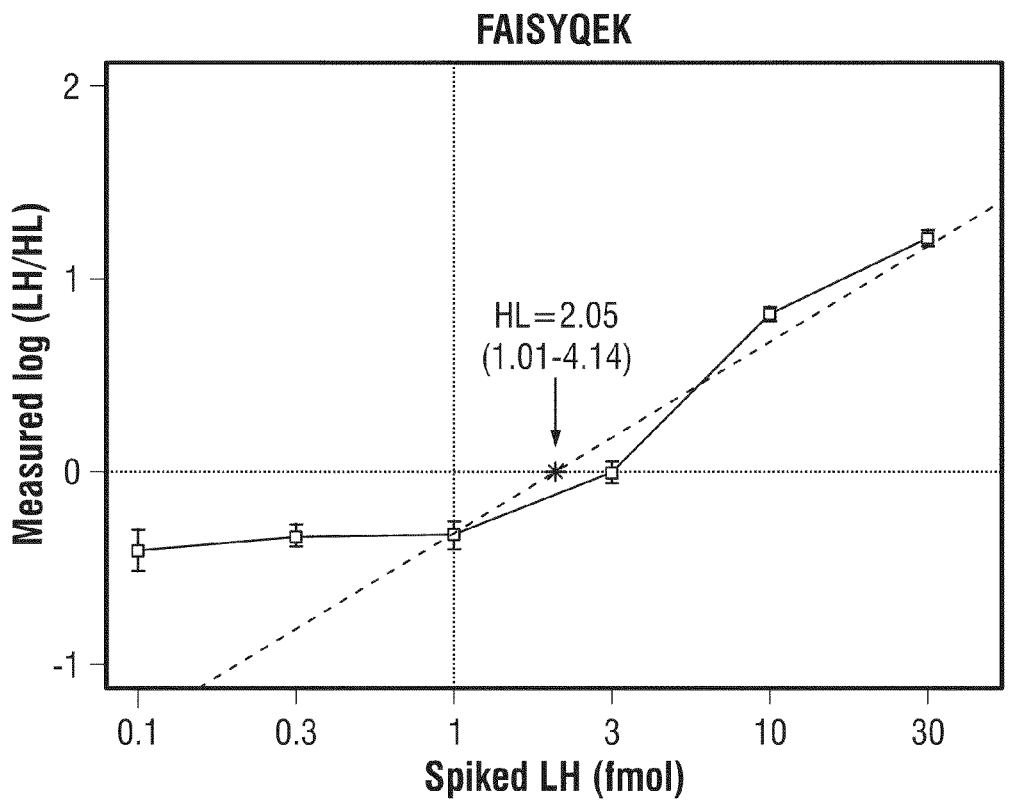
Figure 7E:
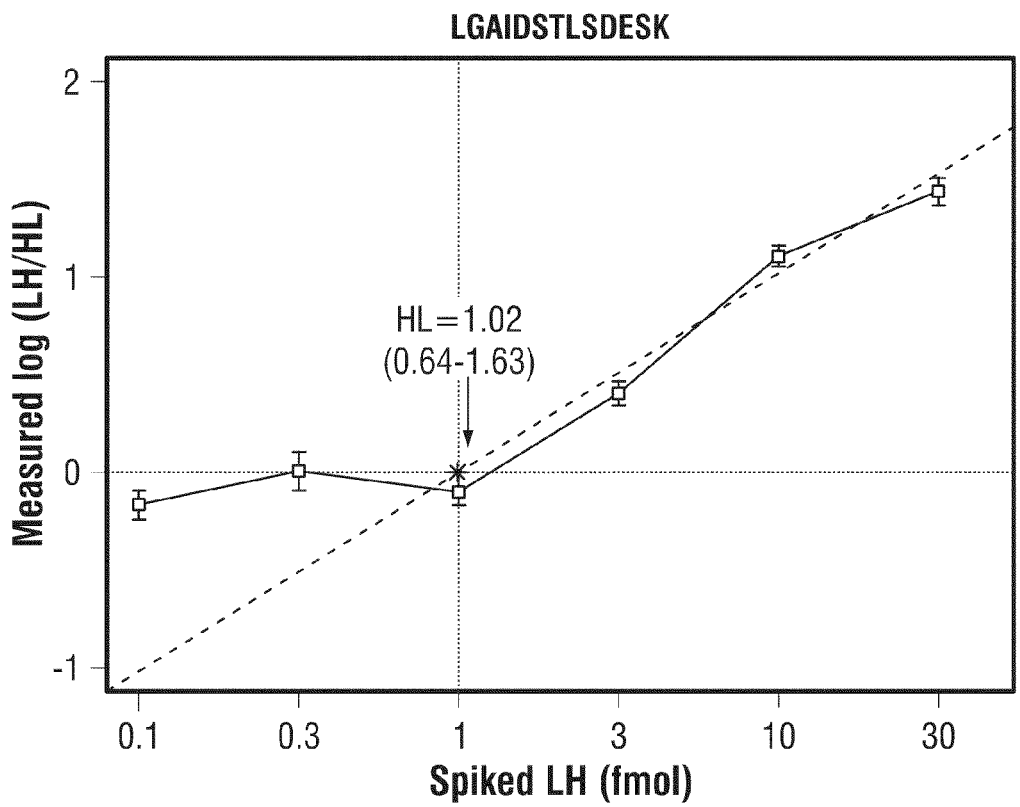
Figure 7F:
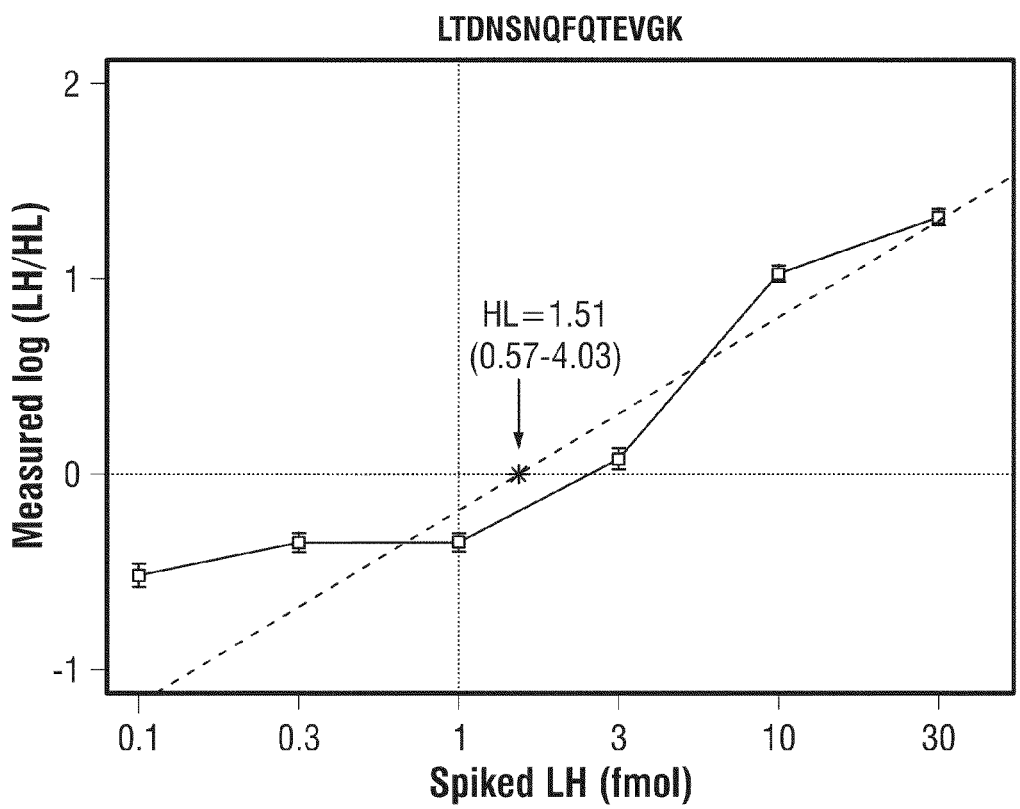
Figure 7G:
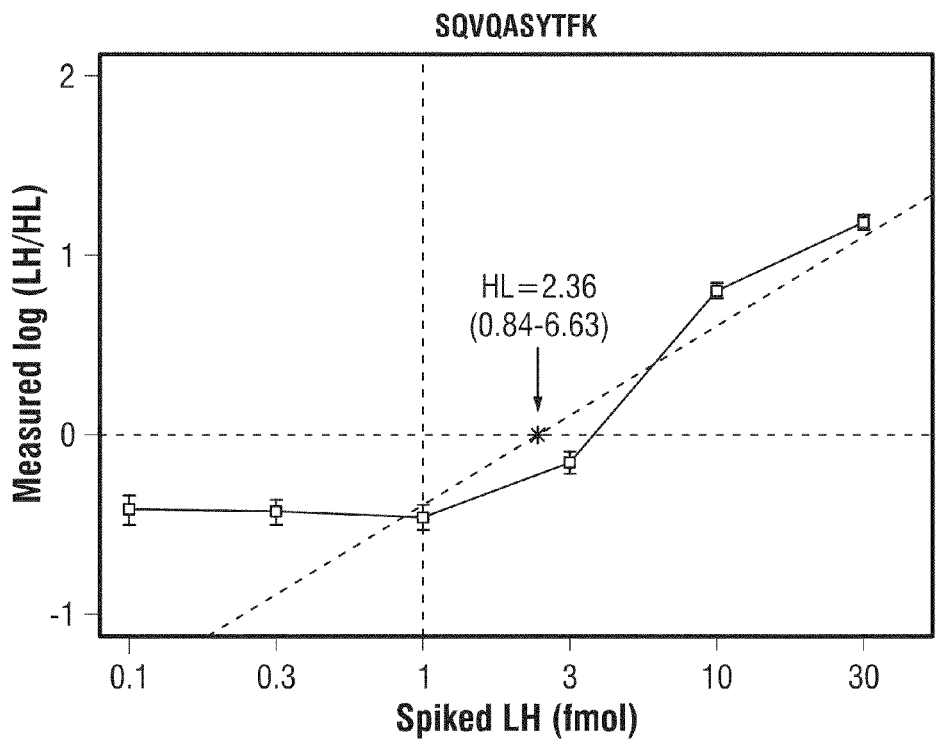
Figure 7H:
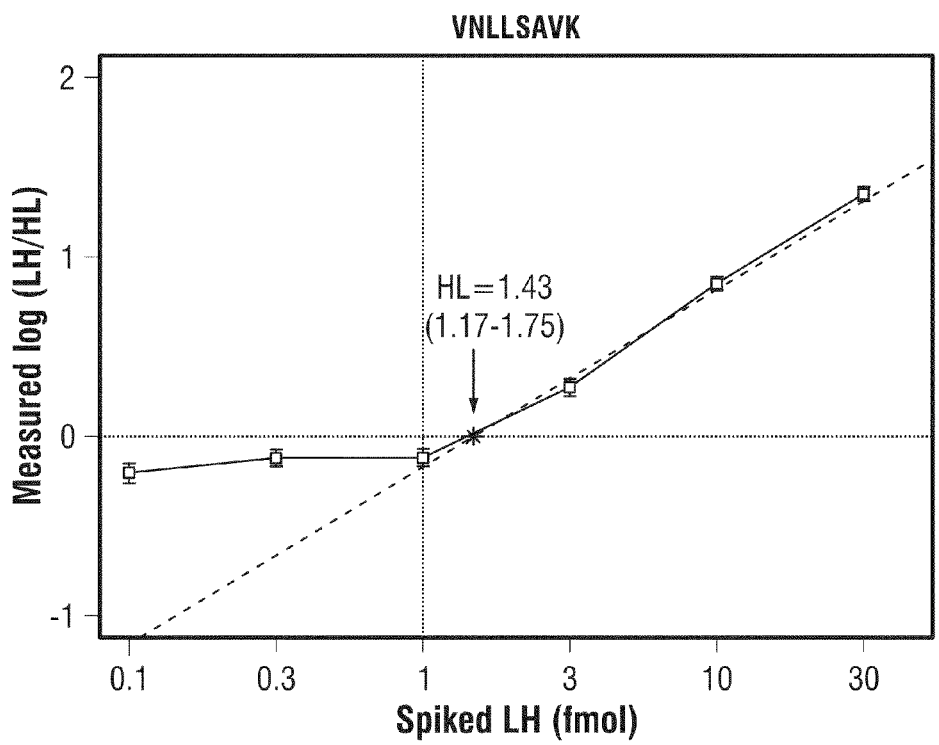

The N-glycopeptide mixture (1 μl) was spiked with LH peptides at quantities of 0.1, 0.3, 1, 3, 10, or 30 fmols, HH peptides (100 fmol), and HL peptides (~3 fmol), to generate expected relative abundances (LH:HL) of 1:30 to 10:1. The measured ratios for all eight peptides are plotted against the spiked amount of the LH peptides (FIG. 6(c); data for each peptide is presented separately in FIG. 7. In samples containing 1 to 30 fmol of the LH peptides, there was good agreement between measured and expected ratios for all eight peptides. For LH peptides spiked in at less than 1 fmol, the correlation was non-linear, suggesting a possible baseline of quantification was reached. For these lower levels, the amount of each LH peptide was estimated based on the linear relationships observed for LH peptide amounts of $\geq 3$ fmol (see FIG. 7). The estimated amount of each LH peptide was between 1 and 3 fmol, which is consistent with the expected amounts of these crude peptides. These results demonstrate that the current iMSTIQ platform accurately and reproducibly quantifies low fmol amounts of target peptides in complex samples.

Example 8 iMSTIQ Abundance Profiling of Targeted Inflammatory Proteins

The iMSTIQ method was used to analyze temporal patterns of protein release from mouse macrophages treated with the inflammatory stimulus, LPS. Release of inflammatory mediators such as cytokines and chemokines by macrophages is a key component of the inflammatory response. Previously, using shotgun proteomics combined with iTRAQ and N-glycopeptide enrichment, a set of proteins that were inducibly released (secreted or proteolytically shed) from macrophages upon treatment with LPS for four hours were identified (see Table 1). In this experiment, the iMSTIQ was used to profile the abundance of these inflammatory proteins in non-enriched samples during a comprehensive time course experiment.

RAW264.7 cells were grown on regular RPMI-1640 media (Invitrogen) containing 10% fetal bovine serum (Invitrogen), 1% Pen/Strep (Invitrogen), and 2 mM L-Glutamine (Invitrogen) at 37° C. with 5% $CO_2$. To activate the cells, the culture media were replaced by OptiMEM (Invitrogen) supplemented with 100 ng/ml LPS (Sigma). Conditioned media were collected at 1, 2, 4, 8, and 18 h. As a control, cells were exposed to OptiMEM supplemented with PBS and media were collected after 18 h. The media were concentrated by centrifugation (3500 rpm×30 min) using Appllo-20 ml concentrators (Orbital Biosciences) and the buffer was exchanged by repeated resuspension in PBS and centrifugation. Equal amounts of protein (15 μg) from each sample were denatured by addition of SDS to 0.2% v/v followed by incubation at 95° C. for 5 min. 2,2,2-Trifluoroethanol (Fluka) was added to 50% v/v, followed by incubation at 60° C. for 30 min. The denatured proteins were then reduced with 5 mM TCEP at 60° C. for 30 min followed by alkylation with 12.5 mM iodoacetamide at 37° C. in the dark for 30 min. The samples were diluted 1:10 with 50 mM TEAB and then digested with trypsin at 1:50 (w/w) enzyme to substrate ratio overnight at 37° C. The digested peptides were desalted on a $C_{18}$ cartridge (Waters), dried by SpeedVac, and de-glycosylated by addition of 1 μl N-glycanase (Prozyme, San Leandro, Calif.) following the manufacturer's protocol.

The resulting peptide mixtures were labeled with the heavy (Δ4) mTRAQ® reagents (Applied Biosystems) to generate the HL peptides according to the manufacturer's protocol. To generate the LH and HH peptides, the 24 selected peptides (14 peptides corresponding to targeted proteins known to be released during inflammation for validation, and 10 peptides corresponding to non-specific proteins) were synthesized via the AQUA® platform (Sigma) carrying heavy ($^{13}C_6^{15}N_2$)-Lys at their C-termini and labeled with light (Δ0) and heavy (Δ4) mTRAQ® reagents to create MSTIQ standard peptides (LH) and ITA index peptides (HH), respectively. The LH (33.3 fmol) and HH (500 fmol) peptides were added to ~3 μg of the digested peptide sample containing the HL peptides described above. The final peptide mixture was purified on MCX μElution plates, dried, and resuspended in 0.1% formic acid prior to LC-MS/MS analysis.

Samples of conditioned media were collected at various times after treatment of macrophages with LPS. As a control, macrophages were treated with PBS and conditioned media was harvested at 18 h. Proteins from the concentrated conditioned media were digested with trypsin, deglycosylated with N-Glycanase, and then labeled with the heavy amine labeling reagent to generate HL peptides. Fourteen peptides corresponding proteins that were found to be inducibly released from macrophages upon LPS treatment (Table 1) were specifically targeted. In addition, 10 peptides corresponding to proteins that are not known as macrophage-released proteins (referred to as non-specific peptides) were targeted. These 24 peptides were synthesized with isotopically heavy lysine at their C-terminus, and then modified with either the light or heavy amine labeling reagents to generate quantification references (LH) or index peptides (HH), respectively. The sample peptide mixtures containing the HL peptides were then spiked with the LH peptides (33.3 fmol each) and the HH peptides (500 fmol each) followed by LTQ-Orbitrap analysis using ITA.

Five MS2 spectra were acquired following each MS1 scan. An intensity threshold of 1000 counts was required to trigger CID. Dynamic exclusion was disabled. MS2 analysis was limited to +2 charged ions using the charge state screening feature. The "Add/Subtract" feature was set to trigger CID on ions with m/z values equal to m/z (index peptide)–3.7500 Da.

All 24 LH peptides used as quantitative reference peptides were unambiguously detected by ISBquant software and validated by manual inspection of their spectra. Ten peptides, including three from the targeted group and seven from the non-specific group (Table 1, Groups 3 and 4 respectively), were not consistently detected in all 6 samples (no HL signals) and thus were not further analyzed. The other 14 peptides, including 11 targeted peptides (Table 1, Group 1) and three non-specific peptides (Table 1, Group 2), were successfully detected and quantified in all of the samples (FIG. 8). In contrast, detection of these peptides by shotgun proteomics methods requires glycopeptide enrichment or fractionation by isoelectric focusing.

FIG. 8 shows absolute quantification (fmol) of each peptide (y-axis) at each monitored time point x-axis). Evaluation of the three non-specific peptides (Group 2) indicated they were present in similar amounts at all measured time points after LPS or PBS treatment (FIG. 8(a)). In contrast, eight of the 11 targeted peptides (Group 1) showed the expected overall pattern of inducible release by macrophages over the time course of LPS treatment (FIG. 8(b)). Proteins corresponding to these peptides include TNFα, Itgb2 (CD18) and Itgam (Mac-1, CD11b). TNFα is a type 1 pro-inflammatory cytokine known to be released by macrophages in response to inflammatory stimuli. Itgb2 and Itgam are components of a heterodimeric complex found on the surface of leukocytes that plays important roles in inflammation, and was previously reported as being shed during an inflammatory response. Unexpectedly, the amounts of the three other targeted peptides, corresponding to Gm885, Raet1, and Cadm1, showed no significant increase after LPS treatment (FIG. 8(c)), suggesting they are not specifically released in response to LPS.

In this example, the iMSTIQ method reproducibly quantified specific sets of proteins from a complex mixture.

TABLE 1

| Gene symbol | Protein | Peptide | Proteins of interest | Detection of HL | Group |
|---|---|---|---|---|---|
| Cadm1 | cell adhesion molecule 1 | FQLLN*FSSSELK | targeted | Yes | 1 |
| Fcgr1 | Fc receptor, IgG, high affinity I | EVVN*ATK | targeted | Yes | |
| Fcgr2b | Fc receptor, IgG, low affinity IIb | SQVQASYTFK | targeted | Yes | |
| Gm885 | predicted gene 885 | VN*VSNLMK | targeted | Yes | |
| H2-k1 | histocompatibility 2, K1, K region | WASVVVPLGK | targeted | Yes | |
| Itgam | integrin alpha M | YLN*FTASEMTSK | targeted | Yes | |
| Itgb2 | integrin beta 2 | LTDNSNQFQTEVGK | targeted | Yes | |
| Raet1 | retinoic acid early transcript 1, A-E | CN*LTIK | targeted | Yes | |
| Sema4d | semaphorin 4D | AAN*YTSSLNLPDK | targeted | Yes | |
| Sorl1 | sortilin-related receptor, LDLR class A repeats-containing | GIGN*WSDSK | targeted | Yes | |
| Tnf | tumor necrosis factor | VNLLSAVK | targeted | Yes | |
| Gm11787 | predicted gene 11787 | GSLLDFLK | non-specific | Yes | 2 |
| Islr | immunoglobulin superfamily containing leucine-rich repeat | FQAFAN*GSLLIPDFGK | non-specific | Yes | |
| P2rx4 | P2X, ligand-gated ion channel 4 purinergic receptor | AAEN*FTLLVK | non-specific | Yes | |
| Alcam | activated leukocyte cell adhesion molecule | N*ATGDYK | targeted | No | 3 |
| Anpep | alanyl (membrane) aminopeptidase | N*ATLVNEADK | targeted | No | |
| Havcr2 | hepatitis A virus cellular receptor 2 | N*VTYQK | targeted | No | |
| B st1 | bone marrow stromal cell antigen 1 | N*CTAIWEAFK | non-specific | No | 4 |
| Chmp2a | chromatin modifying protein 2A | SN*NSMAQAMK | non-specific | No | |
| Dclk1 | doublecortin-like kinase 1 | NVNPN*WSVNVK | non-specific | No | |
| Serpinf1 | serine (or cysteine) peptidase inhibitor, Glade F, member 1 | SSFVAPLEK | non-specific | No | |
| Smc3 | structural maintenace of chromosomes 3 | ALDQFVN*FSEQK | non-specific | No | |
| Vcam1 | vascular cell adhesion molecule 1 | SLEVTFTPVIEDIGK | non-specific | No | |
| Ythdf2 | YTH domain family 2 | VQN*GSVHQK | non-specific | No | |

N*: N-linked glycosylation site replaced by D in synthetic peptides

The invention claimed is:

1. A method of quantifying a peptide of interest in a sample comprising: (a) modifying the peptide of interest at terminus (1) with an isotopically heavy first tag (A*) and at terminus (2) with an isotopically light second tag (B) to form a structure of Formula (I):

A*-Peptide-B  (I);

(b) adding an internal standard to the sample, wherein the internal standard comprises the sequence of the peptide of interest modified at terminus (1) with an isotopically light variant of the first tag (A) and at terminus (2) with an isotopically heavy variant of the second tag (B*), to form a structure of Formula (II):

A-Peptide-B*  (II), wherein the difference in mass between (A*) and (A) is equal to the difference in mass between (B*) and (B) such that the internal standard is isobaric to the modified peptide of interest;

(c) obtaining a first mass spectrum of the sample;

(d) identifying an ion in the first mass spectrum which corresponds to both the modified peptide of interest and the internal standard;

(e) obtaining a second mass spectrum by collision-induced dissociation fragmentation of the ions of both the modified peptide of interest and the internal standard identified in step (d);
(f) comparing the relative intensities of fragment ions of the modified peptide of interest and fragment ions of the internal standard; and
(g) quantifying the peptide of interest based on the comparison from step (f).

2. The method of claim 1, wherein terminus (1) of each peptide is its C-terminus and terminus (2) of each peptide is its N-terminus.

3. The method of claim 1, wherein terminus (1) of each peptide is its N-terminus and terminus (2) of each peptide is its C-terminus.

4. The method of claim 1, wherein terminus (1) of each peptide is its C-terminus, (A) and (A*) are each independently lysine, lysine-alanine, lysine-C(O)CH$_2$-(4-methylpiperazin-1-yl), or arginine, or any isotopically labeled variant thereof, and (B) and (B*) are each independently alanine or —C(O)CH$_2$-(4-methylpiperazin-1-yl), or any isotopically labeled variant thereof.

5. The method of claim 1, wherein terminus (1) of each peptide is its C-terminus, (A) is lysine, lysine-alanine, lysine-($^{13}$C$_3^{15}$N)-alanine, $^{13}$C$_6^{15}$N$_2$-lysine-alanine, lysine-C(O)CH$_2$-(4-methylpiperazin-1-yl), lysine-*C(O)CH$_2$-(4-methylpiperazin-1-yl), $^{13}$C$_6^{15}$N$_2$-lysine-C(O)CH$_2$-(4-methylpiperazin-1-yl), or arginine, and (A*) is $^{13}$C$_6^{15}$N$_2$-lysine, $^{13}$C$_6^{15}$N$_2$-lysine-alanine, $^{13}$C$_6^{15}$N$_2$-lysine-($^{13}$C$_3^{15}$N)-alanine, $^{13}$C$_6^{15}$N$_2$-lysine-C(O)CH$_2$-(4-methylpiperazin-1-yl), $^{13}$C$_6^{15}$N$_2$-lysine-*C(O)CH$_2$-(4-methylpiperazin-1-yl), or $^{15}$N$_4$-arginine.

6. The method of claim 1, wherein terminus (1) of each peptide is its C-terminus, terminus (2) of each peptide is its N-terminus, (A) is lysine, lysine-alanine, lysine-($^{13}$C$_3^{15}$N)-alanine, $^{13}$C$_6^{15}$N$_2$-lysine-alanine, lysine-C(O)CH$_2$-(4-methylpiperazin-1-yl), lysine-*C(O)CH$_2$-(4-methylpiperazin-1-yl), $^{13}$C$_6^{15}$N$_2$-lysine-C(O)CH$_2$-(4-methylpiperazin-1-yl), or arginine, (A*) is $^{13}$C$_6^{15}$N$_2$-lysine, $^{13}$C$_6^{15}$N$_2$-lysine-alanine, $^{13}$C$_6^{15}$N$_2$-lysine-($^{13}$C$_3^{15}$N)-alanine, $^{13}$C$_6^{15}$N$_2$-lysine-C(O)CH$_2$-(4-methylpiperazin-1-yl), $^{13}$C$_6^{15}$N$_2$-lysine-*C(O)CH$_2$-(4-methylpiperazin-1-yl), or $^{15}$N$_4$-arginine, (B*) is ($^{13}$C$_3^{15}$N)-alanine or is derived from an isotopically heavy 2,5-dioxopyrrolidin-1-yl 2-(4-methylpiperazin-1-yl)acetate reagent, and (B) is alanine or an isotopically light variant of the 2,5-dioxopyrrolidin-1-yl 2-(4-methylpiperazin-1-yl)acetate reagent.

7. The method of claim 1, wherein terminus (1) of each peptide is its C-terminus, (A) is lysine-($^{13}$C$_3^{15}$N)-alanine, (A*) is $^{13}$C$_6^{15}$N$_2$-lysine-alanine, (B) is alanine, and (B*) is ($^{13}$C$_6^{15}$N)-alanine.

8. The method of claim 1, wherein terminus (1) of each peptide is its N-terminus, (B) and (B*) are each independently lysine, lysine-alanine, lysine-C(O)CH$_2$-(4-methylpiperazin-1-yl), or arginine, or any isotopically labeled variant thereof, and (A) and (A*) are each independently alanine or —C(O)CH$_2$-(4-methylpiperazin-1-yl), or any isotopically labeled variant thereof.

9. The method of claim 1, wherein terminus (1) of each peptide is its N-terminus, (A*) is ($^{13}$C$_3^{15}$N)-alanine or is derived from an isotopically heavy 2,5-dioxopyrrolidin-1-yl 2-(4-methylpiperazin-1-yl)acetate reagent, and (A) is alanine or an isotopically light variant of the 2,5-dioxopyrrolidin-1-yl 2-(4-methylpiperazin-1-yl)acetate reagent.

10. The method of claim 1, wherein terminus (1) of each peptide is its N-terminus, (A*) is ($^{13}$C$_3^{15}$N)-alanine or is derived from an isotopically heavy 2,5-dioxopyrrolidin-1-yl 2-(4-methylpiperazin-1-yl)acetate reagent, (A) is alanine or an isotopically light variant of the 2,5-dioxopyrrolidin-1-yl 2-(4-methylpiperazin-1-yl)acetate reagent, terminus (2) of each peptide is its C-terminus, (B) is lysine, lysine-alanine, lysine-($^{13}$C$_3^{15}$N)-alanine, $^{13}$C$_6^{15}$N$_2$-lysine-alanine, lysine-C(O)CH$_2$-(4-methylpiperazin-1-yl), lysine-*C(O)CH$_2$-(4-methylpiperazin-1-yl), $^{13}$C$_6^{15}$N$_2$-lysine-C(O)CH$_2$-(4-methylpiperazin-1-yl), or arginine, and (B*) is $^{13}$C$_6^{15}$N$_2$-lysine, $^{13}$C$_6^{15}$N$_2$-lysine-alanine, $^{13}$C$_6^{15}$N$_2$-lysine-($^{13}$C$_3^{15}$N)-alanine, $^{13}$C$_6^{15}$N$_2$-lysine-C(O)CH$_2$-(4-methylpiperazin-1-yl), $^{13}$C$_6^{15}$N$_2$-lysine-*C(O)CH$_2$-(4-methylpiperazin-1-yl), or $^{15}$N$_4$-arginine.

11. The method of claim 1, wherein terminus (1) of each peptide is its N-terminus, (A) is alanine, (A*) is ($^{13}$C$_3^{15}$N)-alanine, terminus (2) of each peptide is its C-terminus, (B) is lysine-($^{13}$C$_3^{15}$N)-alanine, and (B*) is $^{13}$C$_6^{15}$N$_2$-lysine-alanine.

12. A method of detecting a peptide of interest in a sample comprising: (a) modifying the peptide of interest at terminus (1) with a first tag (X) and at terminus (2) with a second tag (Y) to form a structure of Formula (III):

X-Peptide-Y        (III);

(b) adding an index peptide to the sample, wherein the index peptide comprises the sequence of the peptide of interest, modified at terminus (1) with a first tag (X*) and at terminus (2) with a second tag (Y*), to form a structure of Formula (IV):

X*-Peptide-Y*        (IV), wherein each of (X), (X*), (Y), and (Y*) is independently isotopically normal or comprises at least one heavy atom isotope, and are selected such that the difference, x, between a predicted m/z of a parent ion of the index peptide and a predicted m/z for a parent ion of the modified peptide of interest parent ion is large enough that isotopic peaks of the index peptide parent ion are predicted to fall outside an eight m/z unit or smaller collision-induced dissociation isolation window around the predicted m/z of the modified peptide of interest parent ion;
(c) obtaining a first mass spectrum of the sample;
(d) detecting the parent ion for the index peptide in the first mass spectrum;
(e) obtaining a second mass spectrum by collision-induced dissociation fragmentation at a position x Daltons from the index peptide parent ion; and
(f) analyzing the second mass spectrum for fragment ions indicative of the peptide of interest.

13. The method of claim 12, wherein terminus (1) of each peptide is its C-terminus and terminus (2) of each peptide is its N-terminus.

14. The method of claim 12, wherein terminus (1) of each peptide is its N-terminus and terminus (2) of each peptide is its C-terminus.

15. The method of claim 12, wherein both (X) and (Y) are isotopically light.

16. The method of claim 15, wherein (X*) and (Y*) are both isotopically heavy.

17. The method of claim 12, wherein terminus (1) of each peptide is its C-terminus, (X) is lysine, lysine-alanine, $^{13}$C$_6^{15}$N$_2$-lysine-alanine, lysine-($^{13}$C$_3^{15}$N)-alanine, lysine-C(O)CH$_2$-(4-methylpiperazin-1-yl), $^{13}$C$_6^{15}$N$_2$-lysine-C(O)CH$_2$-(4-methylpiperazin-1-yl), lysine-*C(O)CH$_2$-(4-methylpiperazin-1-yl), or arginine, and (X*) is $^{13}$C$_6^{15}$N$_2$-lysine, $^{13}$C$_6^{15}$N$_2$-lysine-alanine, $^{13}$C$_6^{15}$N$_2$-lysine-($^{13}$C$_3^{15}$N)-alanine, $^{13}C_6{}^{15}N_2$-lysine-C(O)CH$_2$-(4-methylpiperazin-1-yl), $^{13}C_6{}^{15}N_2$-lysine-*C(O)CH$_2$-(4-methylpiperazin-1-yl), or $^{15}N_4$-arginine.

18. The method of claim 12, wherein terminus (1) of each peptide is its C-terminus, terminus (2) of each peptide is its N-terminus, (X) is lysine, lysine-alanine, $^{13}C_6{}^{15}N_2$-lysine-alanine, lysine-($^{13}C_3{}^{15}N$)-alanine, lysine-C(O)CH$_2$-(4-methylpiperazin-1-yl), $^{13}C_6{}^{15}N_2$-lysine-C(O)CH$_2$-(4-methylpiperazin-1-yl), lysine-*C(O)CH$_2$-(4-methylpiperazin-1-yl), or arginine, "Y" is alanine or an isotopically light variant of a 2,5-dioxopyrrolidin-1-yl 2-(4-methylpiperazin-1-yl) acetate reagent, (X*) is $^{13}C_6{}^{15}N_2$-lysine, $^{13}C_6{}^{15}N_2$-lysine-alanine, $^{13}C_6{}^{15}N_2$-lysine-($^{13}C_3{}^{15}N$)-alanine, $^{13}C_6{}^{15}N_2$-lysine-C(O)CH$_2$-(4-methylpiperazin-1-yl), $^{13}C_6{}^{15}N_2$-lysine-*C(O)CH$_2$-(4-methylpiperazin-1-yl), or $^{15}N_4$-arginine, and "Y*" is ($^{13}C_3{}^{15}N$)-alanine or is derived from an isotopically heavy 2,5-dioxopyrrolidin-1-yl 2-(4-methylpiperazin-1-yl) acetate reagent.

19. The method of claim 12, wherein terminus (1) of each peptide is its C-terminus, terminus (2) of each peptide is its N-terminus, (X) is $^{13}C_6{}^{15}N_2$-lysine-alanine or lysine-($^{13}C_3{}^{15}N$)-alanine, "Y" is alanine, (X*) is $^{13}C_6{}^{15}N_2$-lysine-($^{13}C_3{}^{15}N$)-alanine, and "Y*" is ($^{13}C_3{}^{15}N$)-alanine.

20. The method of claim 12, wherein terminus (1) of each peptide is its N-terminus, (X*) is ($^{13}C_3{}^{15}N$)-alanine or is derived from an isotopically heavy 2,5-dioxopyrrolidin-1-yl 2-(4-methylpiperazin-1-yl)acetate reagent, and (X) is alanine or an isotopically light variant of the 2,5-dioxopyrrolidin-1-yl 2-(4-methylpiperazin-1-yl)acetate reagent.

21. The method of claim 12, wherein terminus (1) of each peptide is its N-terminus, (X*) is ($^{13}C_3{}^{15}N$)-alanine or is derived from an isotopically heavy 2,5-dioxopyrrolidin-1-yl 2-(4-methylpiperazin-1-yl)acetate reagent, (X) is alanine or an isotopically light variant of the 2,5-dioxopyrrolidin-1-yl 2-(4-methylpiperazin-1-yl)acetate reagent, terminus (2) of each peptide is its C-terminus, "Y*" is $^{13}C_6{}^{15}N_2$-lysine, $^{13}C_6{}^{15}N_2$-lysine-alanine, $^{13}C_6{}^{15}N_2$-lysine-($^{13}C_6{}^{15}N$)-alanine, $^{13}C_6{}^{15}N_2$-lysine-C(O)CH$_2$-(4-methylpiperazin-1-yl), $^{13}C_6{}^{15}N_2$-lysine-*C(O)CH$_2$-(4-methylpiperazin-1-yl), or $^{15}N_4$-arginine, and "Y" is lysine, lysine-alanine, $^{13}C_6{}^{15}N_2$-lysine-alanine, lysine-($^{13}C_3{}^{15}N$)-alanine, lysine-C(O)CH$_2$-(4-methylpiperazin-1-yl), $^{13}C_6{}^{15}N_2$-lysine-C(O)CH$_2$-(4-methylpiperazin-1-yl), lysine-*C(O)CH$_2$-(4-methylpiperazin-1-yl), or arginine.

22. The method of claim 12, wherein terminus (1) of each peptide is its N-terminus, (X*) is ($^{13}C_3{}^{15}N$)-alanine, (X) is alanine, terminus (2) of each peptide is its C-terminus, "Y*" is $^{13}C_6{}^{15}N_2$-lysine-($^{13}C_3{}^{15}N$)-alanine, and "Y" is $^{13}C_6{}^{15}N_2$-lysine-alanine or lysine-($^{13}C_3{}^{15}N$)-alanine.

23. The method of claim 12, wherein x is greater than or equal to +3 Daltons, or is less than or equal to −6 Daltons.

24. The method of claim 12, wherein step (e) further comprises obtaining a second mass spectrum by collision-induced dissociation fragmentation of the index peptide parent ion.

25. A method of analyzing a peptide of interest in a sample comprising:
(a) modifying the peptide of interest at terminus (1) with an isotopically heavy first tag (C*) and at terminus (2) with an isotopically light second tag (D) to form a structure of Formula (V):

C*-Peptide-D                (V);

(b) adding an internal standard to the sample, wherein the internal standard comprises the sequence of the peptide of interest modified at terminus (1) with an isotopically light variant of the first tag (C) and at terminus (2) with an isotopically heavy variant of the second tag (D*), to form a structure of Formula (VI):

C-Peptide-D*                (VI), wherein the difference in mass between C* and C is equal to the difference in mass between D* and D such that the internal standard is isobaric to the modified peptide of interest;
(c) adding an index peptide to the sample, wherein the index peptide comprises the sequence of the peptide of interest,
(I) modified at terminus (1) with an isotopically heavy tag (C*) and at terminus (2) with an isotopically heavy tag (D*) to form a structure of Formula (VII):

C*-Peptide-D*               (VII);

or
(II) modified at terminus (1) with the isotopically light tag (C) and at terminus (2) with the isotopically light tag (D) to form a structure of Formula (VIII):

C-Peptide-D                 (VIII);

and wherein the difference, x, between a predicted m/z of a parent ion of the index peptide and a predicted m/z for a parent ion of the modified peptide of interest is large enough that isotopic peaks of the index peptide parent ion are predicted to fall outside an eight m/z unit or less collision-induced dissociation isolation window around the predicted m/z of the modified peptide of interest parent ion;
(d) obtaining a first mass spectrum of the sample And detecting an ion in the first mass spectrum which corresponds to the index peptide parent ion;
(e) obtaining a second mass spectrum by collision-induced dissociation fragmentation at x m/z units less than a detected m/z for the index peptide parent ion;
analyzing the second mass spectrum for fragment ions indicative of the modified peptide of interest and the internal standard;
(g) comparing the relative intensities of fragment ions of the modified peptide of interest and fragment ions of the internal standard; and
(h) quantifying the peptide of interest based on the comparison from step (g).

26. The method of claim 25, wherein terminus (1) of each peptide is its C-terminus and terminus (2) of each peptide is its N-terminus.

27. The method of claim 25, wherein terminus (1) of each peptide is its C-terminus, (C) and (C*) are each independently lysine, lysine-alanine, lysine-C(O)CH$_2$-(4-methylpiperazin-1-yl), or arginine, or any isotopically labeled variant thereof, and (D) and (D*) are each independently alanine or —C(O)CH$_2$-(4-methylpiperazin-1-yl), or any isotopically labeled variant thereof.

28. The method of claim 25, wherein terminus (1) of each peptide is its C-terminus, (C) is lysine, lysine-alanine, $^{13}C_6{}^{15}N_2$-lysine-alanine, lysine-($^{13}C_3{}^{15}N$)-alanine, lysine-C(O)CH$_2$-(4-methylpiperazin-1-yl), $^{13}C_6{}^{15}N_2$-lysine-C(O)CH$_2$-(4-methylpiperazin-1-yl), lysine-*C(O)CH$_2$-(4-methylpiperazin-1-yl), or arginine, and (C*) is $^{13}C_6{}^{15}N_2$-lysine, $^{13}C_6{}^{15}N_2$-lysine-alanine, $^{13}C_6{}^{15}N_2$-lysine-($^{13}C_3{}^{15}N$)-alanine, $^{13}C_6{}^{15}N_2$-lysine-C(O)CH$_2$-(4-methylpiperazin-1-yl), $^{13}C_6{}^{15}N_2$-lysine-*C(O)CH$_2$-(4-methylpiperazin-1-yl), or $^{15}N_4$-arginine.

29. The method of claim 25, wherein terminus (1) of each peptide is its C-terminus, terminus (2) of each peptide is its N-terminus, (C) is lysine, lysine-alanine, $^{13}C_6{}^{15}N_2$-lysinealanine, lysine-($^{13}C_3^{15}N$)-alanine, lysine-C(O)CH$_2$-(4-methylpiperazin-1-yl), $^{13}C_6^{15}N_2$-lysine-C(O)CH$_2$-(4-methylpiperazin-1-yl), lysine-*C(O)CH$_2$-(4-methylpiperazin-1-yl), or arginine, (C*) is $^{13}C_6^{15}N_2$-lysine, $^{13}C_6^{15}N_2$-lysine-alanine, $^{13}C_6^{15}N_2$-lysine-($^{13}C_3^{15}N$)-alanine, $^{13}C_6^{15}N_2$-lysine, $^{13}C_6^{15}N_2$-lysine-alanine, $^{13}C_6^{15}N_2$-lysine-($^{13}C_3^{15}N$)-alanine, $^{13}C_6^{15}N_2$-lysine-C(O)CH$_2$-(4-methylpiperazin-1-yl), $^{13}C_6^{15}N_2$-lysine-*C(O)CH$_2$-(4-methylpiperazin-1-yl), or $^{15}N_4$-arginine, (D*) is ($^{13}C_3^{15}N$)-alanine or is derived from an isotopically heavy 2,5-dioxopyrrolidin-1-yl 2-(4-methylpiperazin-1-yl)acetate reagent, and (D) is alanine or an isotopically light variant of the 2,5-dioxopyrrolidin-1-yl 2-(4-methylpiperazin-1-yl)acetate reagent.

30. The method of claim 25, wherein terminus (1) of each peptide is its C-terminus, terminus (2) of each peptide is its N-terminus, (C) is lysine-($^{13}C_3^{15}N$)-alanine, (D) is alanine, (C*) in Formula (V) is $^{13}C_6^{15}N_2$-lysine-alanine, (C*) in Formula (VII) is $^{13}C_6^{15}N_2$-lysine-($^{13}C_3^{15}N$)-alanine, and (D*) is ($^{13}C_3^{15}N$)-alanine.

31. The method of claim 25, wherein terminus (1) of each peptide is its N-terminus, (D) and (D*) are each independently lysine, lysine-alanine, lysine-C(O)CH$_2$-(4-methylpiperazin-1-yl), or arginine, or any isotopically labeled variant thereof, and (C) and (C*) are each independently alanine or —C(O)CH$_2$-(4-methylpiperazin-1-yl), or any isotopically labeled variant thereof.

32. The method of claim 25, wherein terminus (1) of each peptide is its N-terminus, (C*) is ($^{13}C_3^{15}N$)-alanine or is derived from an isotopically heavy 2,5-dioxopyrrolidin-1-yl 2-(4-methylpiperazin-1-yl)acetate reagent, and (C) is alanine or an isotopically light variant of the 2,5-dioxopyrrolidin-1-yl 2-(4-methylpiperazin-1-yl)acetate reagent.

33. The method of claim 25, wherein terminus (1) of each peptide is its N-terminus, (C*) is ($^{13}C_3^{15}N$)-alanine or is derived from an isotopically heavy 2,5-dioxopyrrolidin-1-yl 2-(4-methylpiperazin-1-yl)acetate reagent, (C) is alanine or an isotopically light variant of the 2,5-dioxopyrrolidin-1-yl 2-(4-methylpiperazin-1-yl)acetate reagent, terminus (2) of each peptide is its C-terminus, (D*) is $^{13}C_6^{15}N_2$-lysine, $^{13}C_6^{15}N_2$-lysine-alanine, $^{13}C_6^{15}N_2$-lysine-($^{13}C_3^{15}N$)-alanine, $^{13}C_6^{15}N_2$-lysine-C(O)CH$_2$-(4-methylpiperazin-1-yl), $^{13}C_6^{15}N_2$-lysine-*C(O)CH$_2$-(4-methylpiperazin-1-yl), or $^{15}N_4$-arginine, and (D) is lysine, lysine-alanine, $^{13}C_6^{15}N_2$-lysine-alanine, lysine-($^{13}C_3^{15}N$)-alanine, lysine-C(O)CH$_2$-(4-methylpiperazin-1-yl), $^{13}C_6^{15}N_2$-lysine-C(O)CH$_2$-(4-methylpiperazin-1-yl), lysine-*C(O)CH$_2$-(4-methylpiperazin-1-yl), or arginine.

34. The method of claim 25, wherein terminus (1) of each peptide is its N-terminus, (C*) is ($^{13}C_3^{15}N$)-alanine, (C) is alanine, terminus (2) of each peptide is its C-terminus, (D*) in Formula (VI) is $^{13}C_6^{15}N_2$-lysine-alanine, (D*) in Formula (VII) is $^{13}C_6^{15}N_2$-lysine-($^{13}C_3^{15}N$)-alanine, and (D) is lysine-($^{13}C_3^{15}N$)-alanine.

35. The method of claim 25, wherein step (e) further comprises obtaining a second mass spectrum by collision-induced dissociation fragmentation of the index peptide parent ion.

* * * * *